(12) United States Patent
Haines et al.

(10) Patent No.: US 7,803,613 B2
(45) Date of Patent: *Sep. 28, 2010

(54) POSTWEANING MULTISYSTEMIC WASTING SYNDROME AND PORCINE CIRCOVIRUS FROM PIGS

(75) Inventors: Deborah Haines, Saskatoon (CA); Gordon Allan, Belfast (GB); John Ellis, Saskatoon (CA); Brian Meehan, Belfast (GB); Edward Clark, Saskatoon (CA); Lori Hassard, Saskatoon (CA); John Harding, Humboldt (CA); Catherine Elisabeth Charreyre, Saint-Laurent de Mure (FR); Gilles Emile Chappuis, Lyons (FR); Francis McNeilly, Newtonards (GB); Li Wang, Grand Prairie, TX (US); Lorne A. Babiuk, Saskatoon (CA); Andrew A. Potter, Saskatoon (CA); Philip Willson, Saskatoon (CA)

(73) Assignee: Merial SAS, Lyons (FR)

( * ) Notice: Subject to any disclaimer, the term of this patent is extended or adjusted under 35 U.S.C. 154(b) by 192 days.

This patent is subject to a terminal disclaimer.

(21) Appl. No.: 11/485,525

(22) Filed: Jul. 12, 2006

(65) Prior Publication Data

US 2006/0292177 A1    Dec. 28, 2006

Related U.S. Application Data

(60) Continuation of application No. 10/653,849, filed on Sep. 2, 2003, now Pat. No. 7,192,594, which is a continuation-in-part of application No. 10/334,245, filed on Dec. 31, 2002, now Pat. No. 7,144,698, which is a continuation of application No. 09/935,428, filed on Aug. 20, 2001, now abandoned, which is a continuation of application No. 09/209,961, filed on Dec. 10, 1998, now abandoned, application No. 11/485,525, which is a continuation-in-part of application No. 09/884,514, filed on Jun. 19, 2001, now Pat. No. 6,660,272, which is a division of application No. 09/161,092, filed on Sep. 25, 1998, now Pat. No. 6,391,314, which is a continuation-in-part of application No. 09/082,558, filed on May 21, 1998, now Pat. No. 6,368,601, application No. 11/485,525, which is a continuation-in-part of application No. 09/680,228, filed on Oct. 6, 2000, now abandoned, which is a continuation-in-part of application No. 09/583,350, filed on May 31, 2000, now Pat. No. 6,517,843, application No. 11/485,525, which is a continuation-in-part of application No. 09/784,962, filed on Feb. 16, 2001, now Pat. No. 6,953,581, which is a division of application No. 09/347,594, filed on Jul. 1, 1999, now Pat. No. 6,217,883.

(60) Provisional application No. 60/069,750, filed on Dec. 16, 1997, provisional application No. 60/069,233, filed on Dec. 11, 1997, provisional application No. 60/151,564, filed on Aug. 31, 1999.

(30) Foreign Application Priority Data

| Oct. 3, 1997 | (FR) | 97 12382 |
| Jan. 22, 1998 | (FR) | 98 00873 |
| Mar. 22, 1998 | (FR) | 98 03707 |
| Jul. 6, 1998 | (FR) | 98 08777 |

(51) Int. Cl.
*C12N 5/00* (2006.01)
*A61K 39/12* (2006.01)

(52) U.S. Cl. ............... 435/320.1; 536/23.72; 424/204.1
(58) Field of Classification Search ...................... None
See application file for complete search history.

(56) References Cited

U.S. PATENT DOCUMENTS

| 5,498,413 A * | 3/1996 | Casal Alvarez et al. .. 424/233.1 |
| 6,207,165 B1 | 3/2001 | Audonnet et al. |
| 6,217,883 B1 | 4/2001 | Allan et al. |
| 6,368,601 B1 | 4/2002 | Allan et al. |
| 6,391,314 B1 | 5/2002 | Allan et al. |
| 6,703,023 B1 | 3/2004 | Jestin et al. |

FOREIGN PATENT DOCUMENTS

| EP | 1386617 B1 | 3/2008 |
| FR | 9715396 | * 12/1997 |
| FR | 2772047 | 6/1999 |
| WO | WO 96/40931 | 12/1996 |
| WO | WO 99/18214 | 4/1999 |
| WO | WO 99/29717 | 6/1999 |
| WO | WO 00/77216 | 12/2000 |

OTHER PUBLICATIONS

Verma et al. Nature, 1997, vol. 389, pp. 239-242.*
Orkin et al. Report and Recommendation of the Panel to Assess the NIH Investment in Research on Gene Therapy, NIH, 1995, 37 pages from internet printout; http://www4.od.nih.gov/oba/RAC/panelrep.pdf.*
Albina et al., La Semaine Veterinaire des Filieres, No. 26, Nov. 30, 1996, pp. 1-2.
Allan et al., Vet. Immunol. Immunopathol., vol. 43 (1994), pp. 357-371.
Allan et al., Vet. Micro., vol. 44 (1995), pp. 49-64.
Allan et al., "Isolation of Porcine, Circovirus-Like Viruses From Pigs With a Wasting Disease in the USA and Europe", J. Vet. Diagn. Invest. 10:3-10 (1998).
Allan et al., 2000. J. Vet. Diagn. Invest. 12: 3-14.
Allan et al., 2000. Veterinary Record. 147(6): 170-171.

(Continued)

*Primary Examiner*—Stacy B Chen
(74) *Attorney, Agent, or Firm*—Judy Jarecki-Black; Ruoying Chen; Merial Limited

(57) ABSTRACT

The cloning of a novel PCVII viral genome is described as is expression of proteins derived from the PCVII genome. These proteins can be used in vaccine compositions for the prevention and treatment of PCVII infections, as well as in diagnostic methods for determining the presence of PCVII infections in a vertebrate subject. Polynucleotides derived from the viral genome can be used as diagnostic primers and probes.

18 Claims, 12 Drawing Sheets

OTHER PUBLICATIONS

Clark, American Association of Swine Practioners, 1997, pp. 499-501.
Daft et al., 39$^{th}$ Annual Meeting of American Association of Veterinary Laboratory Diagnosticians, Oct. 12-18, 1996.
Database WPI, Section Ch, Week 9529, Derwent Publications Ltd., London, GB; An 95-222945 XP002099703 & SU 1 538 305 A (Veterinary Preparations Res Inst), Dec. 15, 1994.
Dedet, La Semaine Veterinaire, May 24, 1997, p. 54.
Ellis et al., Jan. 1988, Isolation of circovirus from lesions of pigs with postwearing multi systemic wasting syndrome. Canadian Journal vol. 39 (1): 44-51. Abstract Only.
Ellis et al., "Isolation of Circovirus From Lesions of Pigs With Postweaving Multisystemic Wasting Syndrome", Can. Vet. J. 39:44-51 (1998).
Ellis, et al., Coinfection by Porcine Circoviruses and Porcine Parvovirus in Pigs with Naturally Acquired Postweaning Multisystemic Wasting Syndrome. 2000, Journal of Veterinary Diagnostic Investigation, vol. 12, No. 1, pp. 21-27.
Hamel et al., Database EMBL/Genbank/DDBJ, Sep. 26, 1997.
Hamel et al., "Nucleotide Sequence for Porcine Circovirus Associated With Postweaving Multisystemic Wasting Syndrome in Pigs", Journal of Virology 72(6):5262-5267 (1998).
Harding et al., American Association of Swine Practioners, 1997, p. 503.
Isumida, et al., Establishment of the Attenuated Strain of Porcine Parvovirus of the Live Vaccine and its Biological-Immunological Characteristics, 1996, Japanese Veterinary Science, vol. 48, No. 2, pp. 293-303.
Krakowa et al. Viral Immunology. 2002; 15(4): 567-582.
Krakowa et al. Vet. Pathology. 2001; 38:31-42.
Mahé et al., "Differential Recognition of OFR 2 Protein from Type 1 and Type 2 Porcine Circoviruses and Identification of Immunorelevant Epitopes", Journal of General Virology 81:1815-1824 (2000).
Mankertz et al., "Porcine Circovirus Complete Genome", EMBL Sequence Database XP-002104869 (1996).
Mankertz et al., "Mapping and Characterization of the Origin of DNA Replication of Porcine Circovirus", Journal of General Virology 71(3):2562-2566 (1997).
Meehan B.M. et al., "Sequence of Porcine Circovirus DNA; Affinities with Plant Circoviruses", Journal of General Virology 78(1):221-227 (1997).
Meehan B.M. et al., "Characterization of Novel Circovirus DNA's Associated with Wasting Syndrome in Pigs", Journal of General Virology 79(9):2171-2719 (1998).
Meehan et al., "Putative PCV Replication-Associated Protein (REP)", EMBL Sequence Database XP 002104867 (1997).
Meehan et al., "Porcine Circovirus Complete Genome", EMBL Sequence Database XP-002104868 (1997).
Morozov et al., "Detection of a Novel Strain of Porcine Circovirus in Pigs with Postweaving Multisystemic Wasting Syndrome", Journal of Clinical Microbiology 36(9):2535-2541 (1998).
Nawagtigul et al., "Open Reading Frame 2 of Porcine Circovirus Type 2 Encodes a Major Capsid Protein", Journal of General Virology 81:2281-2287 (2000).
Nayar et al., "Detection and Characterization of Porcine Circovirus Associated with Postweaning Multisystemic Wasting Syndrome in Pigs", Canadian Veterinary Journal-Revue Veterinaire Canadienne 38(3):385-386 (1997).
Segales et al., Veterinary Record, Dec. 6, 1997, pp. 600-601.
Tischer et al., "Studies on Epideniology and Pathogenicity of Porcine Circovirus", Arch. Virol. 91:271-276 (1986).
Todd et al., "Comparison of Three Animal Viruses with Circular Single-Stranded DNA Genomes", Arch. Virol. 117:129-135 (1991).
Vannier, et al., Study of the Efficacy of an Inactivated Virus Vaccine Against Porcine Parvovirus, 1996, Ann. Rech. Vet. vol. 17, No. 4, pp. 425-432.
West et al. 1999. J. Vet. Diagn. Invest. 11: 530-532.
Young. Parvoviruses. In B.N. Fields et al. (ed.), Fields Virology 3$^{rd}$ ed. Philadelphia: Lippencott-Raven Publishers; 1996: 2213.
Voget et al., "Clinical Microbiology Reviews" vol. 8, No. 3, pp. 406-410 (1995).
John Ellis et al., "Isolation of circovirus from lesions of pigs with postweaning multisystemic wasting syndrome", Can Vet J, vol. 39, Jan. 1998, pp. 44-51.
"Automated DNA Sequencing, Chemistry Guide" ABI-Prism, Applied Biosystems product manual; applicable to automated sequencers ABI Prism 310, 377 and 372, 2000, pp. 13-14.
Tischer, et al., Arch. Viral., 96, 39-57, 1987.
AF055391, AF055392, AF055393 and AF055394 and Genbank revision histories, (1998).
Office Action dated Aug. 13, 2003, in relation to application No. 02017134.4 (with summary in English).
EPO file wrappers relating to parent application No. 98946547.1: Letter to the Examiner, dated Oct. 23, 2002 (with summary in English).
Lecann, et al., Vet. Rec., 141 (25), 660, Dec. 20-27, 1997.
Allen, et al., Vet. Rec., 142(17), 467-468, Apr. 25, 1998.
Allan, et al., Vet. Microbiol., 66, 115-123, 1999.
Krakowka, vet. Pathol., 37, 254-263, 2000.
Harding, vet. Microbiol., 98, 131-135, 2004.
Todd, et al., J Gen. Virol., 71 :819-823, 1990.
Todd, et al., J Clin. Microb., 29 (5):933-939, May 1991.
Hamel, et al., Canadian Journal of veterinary research, 64, 44-52, 2000.
Walker et al., J. vet Diagn. Invest., 12, 400-405, 2000.
GenBank Accession No. AF027217; Dec. 17, 1997.
GenBank Accession No. AF027217; May 14, 1998.
Gopi et al., "Detection and Characterization of Porcine Circovirus Associated With Postweaving Multisystemic Wasting Syndrome Pigs", Can Vet. J. 38:385-386 (1997).

* cited by examiner

```
  1   accagcgcacttcggcagcggcagcacctcggcagcacctcagcagcaacatgcccagca   60
      tggtcgcgtgaagccgtcgccgtcgtggagccgtcgtggagtcgtcgttgtacgggtcgt
1                                                            M  P  S  K 61   agaagaatggaagaagcggaccccaaccacataaaaggtgggtgttcacgctgaataatc  120
      tcttcttaccttcttcgcctggggttggtgtatttccacccacaagtgcgacttattag
1      K  N  G  R  S  G  P  Q  P  H  K  R  W  V  F  T  L  N  N  P 121   cttccgaagacgagcgcaagaaaatacgggagctcccaatctccctatttgattattta   180
      gaaggcttctgctcgcgttcttttatgccctcgagggttagagggataaactaataaaat
1      S  E  D  E  R  K  K  I  R  E  L  P  I  S  L  F  D  Y  F  I 181   ttgttggcgaggagggtaatgaggaaggacgaacacctcacctccaggggttcgctaatt  240
      aacaaccgctcctcccattactccttcctgcttgtggagtggaggtccccaagcgattaa
1      V  G  E  E  G  N  E  E  G  R  T  P  H  L  Q  G  F  A  N  F 241   ttgtgaagaagcaaacttttaataaagtgaagtggtatttgggtgcccgctgccacatcg  300
      aacacttcttcgtttgaaaattatttcacttcaccataaacccacgggcgacggtgtagc
1      V  K  K  Q  T  F  N  K  V  K  W  Y  L  G  A  R  C  H  I  E 301   agaaagccaaaggaactgatcagcagaataaagaatattgtagtaaagaaggcaacttac  360
      tctttcggtttccttgactagtcgtcttatttcttataacatcatttcttccgttgaatg
1      K  A  K  G  T  D  Q  Q  N  K  E  Y  C  S  K  E  G  N  L  L
2                                                                   *

361   ttattgaatgtggagctcctcgatctcaaggacaacggagtgacctgtctactgctgtga  420
      aataacttacacctcgaggagctagagttcctgttgcctcactggacagatgacgacact
1      I  E  C  G  A  P  R  S  Q  G  Q  R  S  D  L  S  T  A  V  S
2   K  N  F  T  S  S  R  S  R  L  S  L  P  T  V  Q  R  S  S  H
3                                      *  P  C  R  L  S  R  D  V  A  T 421   gtaccttgttggagagcgggagtctggtgaccgttgcagagcagcaccctgtaacgtttg  480
      catggaacaacctctcgccctcagaccactggcaacgtctcgtcgtgggacattgcaaac
1      T  L  L  E  S  G  S  L  V  T  V  A  E  Q  H  P  V  T  F  V
2      T  G  Q  Q  L  A  P  T  Q  H  G  N  C  L  L  V  R  Y  R  K
3   L  V  K  N  S  L  P  L  R  T  V  T  A  S  C  C  G  T  V  N 481   tcagaaatttccgcgggctggctgaacttttgaaagtgagcgggaaaatgcagaagcgtg  540
      agtctttaaaggcgcccgaccgacttgaaaactttcactcgcccttttacgtcttcgcac
1      R  N  F  R  G  L  A  E  L  L  K  V  S  G  K  M  Q  K  R  D
2      D  S  I  E  A  P  Q  S  F  K  Q  F  H  A  P  F  H  L  L  T
3   T  L  F  K  R  P  S  A  S  S  K  F  T  L  P  F  I  C  F  R 541   attggaagaccaatgtacacgtcattgtggggccacctgggtgtggtaaaagcaaatggg  600
      taaccttctggttacatgtgcagtaacaccccggtggacccacaccattttcgtttaccc
4                M  Y  T  S  L  W  G  H  L  G  V  V  K  A  N  G
1      W  K  T  N  V  H  V  I  V  G  P  P  G  C  G  K  S  K  W  A
2      I  P  L  G  I  Y  V  D  N  H  P  W  R  P  T  T  F  A  F  P
3      S  Q  F  V  L  T  C  T  M 601   ctgctaattttgcagacccggaaaccacatactggaaaccacctagaaacaagtggtggg  660
      gacgattaaaacgtctgggcctttggtgtatgacctttggtggatctttgttcaccaccc
4      L  L  I  L  Q  T  R  K  P  H  T  G  N  H  L  E  T  S  G  G
1         A  N  F  A  D  P  E  T  T  Y  W  K  P  P  R  N  K  W  D
2      S  S  I  K  C  V  R  F  G  C  V  P  F  W  R  S  V  L  P  P
```

*FIG. 2A*

```
      661  atggttaccatggtgaagaagtggttgttattgatgactttttatggctggctgccgtggg   720
           taccaatggtaccacttcttcaccaacaataactactgaaaataccgaccgacggcaccc
   4        M  V  T  M  V  K  K  W  L  L  L  M  T  F  M  A  G  C  R  G
   1          G  Y  H  G  E  E  V  V  V  I  D  D  F  Y  G  W  L  P  W  D
   2             I  T  V  M 721  atgatctactgagactgtgtgatcgatatccattgactgtagagactaaaggtggaactg   780
           tactagatgactctgacacactagctataggtaactgacatctctgatttccaccttgac
   4        M  I  Y  *
   1           D  L  L  R  L  C  D  R  Y  P  L  T  V  E  T  K  G  G  T  V 781  tacctttttggcccgcagtattctgattaccagcaatcagaccccgttggaatggtact    840
           atggaaaaaaccgggcgtcataagactaatggtcgttagtctgggcaaccttaccatga
   1           P  F  L  A  R  S  I  L  I  T  S  N  Q  T  P  L  E  W  Y  S 841  cctcaactgctgtcccagctgtagaagctctctatcggaggattacttccttggtatttt   900
           ggagttgacgacagggtcgacatcttcgagagatagcctcctaatgaaggaaccataaaa
   1           S  T  A  V  P  A  V  E  A  L  Y  R  R  I  T  S  L  V  F  W 901  ggaagaatgctacaaaacaatccacggaggaagggggccagttcgtcacccttccccccc   960
           ccttcttacgatgtttttgttaggtgcctcctttccccggtcaagcagtgggaagggggg
   1           K  N  A  T  K  Q  S  T  E  E  G  G  Q  F  V  T  L  S  P  P 961  catgccctgaatttccatatgaaataaattactgagtcttttttatcacttcgtaatggt  1020
           gtacgggacttaaaggtatactttatttaatgactcagaaaaaatagtgaagcattacca
   5                                                                  M  V
   1           C  P  E  F  P  Y  E  I  N  Y  *

1021  ttttattattcatttagggttcaagtggggggtctttaagattaaattctctgaattgta  1080
           aaaataataagtaaatcccaagttcaccccccagaaattctaatttaagagacttaacat
   5        F  I  I  H  L  G  F  K  W  G  V  F  K  I  K  F  S  E  L  Y
   6          *  P  E  L  P  P  D  K  L  N  F  E  R  F  Q 1081  catacatggttacacggatattgtagtcctggtcgtatttactgttttcgaacgcagtgc  1140
           gtatgtaccaatgtgcctataacatcaggaccagcataaatgacaaaagcttgcgtcacg
   5        I  H  G  Y  T  D  I  V  V  L  V  V  F  T  V  F  E  R  S  A
   6        V  Y  M  T  V  R  I  N  Y  D  Q  D  Y  K  S  N  E  F  A  T 1141  cgaggcctacgtggtccacatttccagagggtttgtagcctcagccaaagctgattcctt   1200
           gctccggatgcaccaggtgtaaaggtctccaaacatcggagtcggtttcgactaaggaaa
   5        E  A  Y  V  V  H  I  S  R  G  L  *
   6        G  L  G  V  H  D  V  N  G  S  T  Q  L  R  L  W  L  Q  N  R 1201  tgttatttggttggaagtaatcaatagtggagtcaagaacaggtttgggtgtgaagtaac  1260
           acaataaaccaaccttcattagttatcacctcagttcttgtccaaacccacacttcattg
   6           K  N  N  P  Q  F  Y  D  I  T  S  D  L  V  P  K  P  T  F  Y 1261  gggagtggtaggagaagggttgggggattgtatggcgggaggagtagtttacatatggt   1320
           ccctcaccatcctcttcccaaccccctaacataccgccctcctcatcaaatgtataccca
   6           R  S  H  Y  S  F  P  Q  P  I  T  H  R  S  S  Y  N  V  Y  P 1321  cataggttagggctgtggcctttgttacaaagttatcatctaaaataacagcagtggagc   1380
           gtatccaatcccgacaccggaaacaatgtttcaatagtagattttattgtcgtcacctcg
   6        D  Y  T  L  A  T  A  K  T  V  F  N  D  D  L  I  V  A  T  S
```

*FIG. 2B*

```
1381  ccactccccctatcaccctggtgatggggagcaaggccagaattcaacctttc  1440
      ggtgagggatagtgggaccactaccccctcgttccggtcttaagttgaattgaaag
      G  V  G  R  D  G  Q  T  I  P  S  C  P  W  F  E  V  K  V  K 1441  ttattctgtagtattcaaaggtgtatagagatttgttcccccctcccggggaacaa  1500
      aataagacatcataagtttccatatctctaaaacaaccaggggggaggcccccttgtt
      R  I  R  Y  Y  E  F  P  I  S  I  K  N  T  G  G  P  P  V 1501  agtcgtcaatttaaatctcatcatgtccaccgcccaggagggcgttgtgactgtgtac  1560
      tcagcagttaaaattagagtagtacagtggcgggtcctcccgcaacactgacaccatg
      F  D  D  I  K  F  R  M  M  D  V  A  W  S  P  T  T  V  T  T 1561  gcttgacagtatatccgaaggtgcgggagaggcggtgttgaagatgccatttttcctc  1620
      cgaactgtcatataggcttccacgccctccgccacaacttctacgtaaaaaggaag
      R  K  V  T  Y  G  F  T  R  S  L  R  T  N  F  I  G  N  K  R 1621  tccaacgtagcggtggcggggtggacgagcaggggcggcgccgccgcctcctagaccggtt  1680
      aggttgcatcgccaccgccccacctgctccgcccgccggcggcggaggatctgccaa
      R  W  R  Y  R  H  R  P  H  V  L  W  P  R  R  R  L  I  Q  G 1681  gatggctgcgggggcggtgtcttctgcgtaacgcctccttggatacgtcatagctg  1740
      ctaccgacgcccccgccattgcggagaacgccatgcggaggaaccatgcagtatcgac
      L  H  S  R  P  R  H  R  R  R  R  Y  R  R  R  P  Y  T  M 1741  aaaacgaaaagaagtgcgctgtaagtatt  1800
      tttgcttttcttcacgcgacattcataa
```

FIG. 2C

```
              10        20        30        40        50        60
     MPSKKNGRSGPQPHKRWVFTLNNPSEDERKKIRELPISLFDYFIVGEEGNEEGRTPHLQG
     :::::    :::::::::::::::::.:...::::::::::::::. :::: :::::::::
     MPSKK---SGPQPHKRWVFTLNNPSEEEKNKIRELPISLFDYFVCGEEGLEEGRTPHLQG
          10        20        30        40        50

70        80        90       100       110       120
     FANFVKKQTFNKVKWYLGARCHIEKAKGTDQQNKEYCSKEGNLLIECGAPRSQGQRSDLS
     ::::.:::::::::::::.::::::::::::::::::::::::..:::::::::..:::::
     FANFAKKQTFNKVKWYFGARCHIEKAKGTDQQNKEYCSKEGHILIECGAPRNQGKRSDLS
        60        70        80        90       100       110

130       140       150       160       170       180
     TAVSTLLESGILVTVAKQHPVTFVKNFRGLAELLKVSGKMQKRDWKTNVHFIVGPPGCGK
     ::::::::.: ::::::.: :::.:.::::::::::::::::::::::::'::  :: :::::::::
     TAVSTLLETGSLVTVAEQFPVTYVRNFRGLAELLKVSGKMQQRDWKTAVHVIVGPPGCGK
        120       130       140       150       160       170

190       200       210       220       230       240
     SKWAANFANPETTYWKPPKNKWWDGYHGEKVVVIDDFYGWLPWDDLLRLCDRYPLTVKTK
     :..:: :::::.:.  ::::: .::::::::::.:::.:::::::::::::::::::::::.::
     SQWARNFAEPRDTYWKPSRNKWWDGYHGEEVVVLDDFYGWLPWDDLLRLCDRYPLTVETK
        180       190       200       210       220       230

250       260       270       280       290
     GGTVPFLARSILITSNQTPLEWYSSTAVPAVEALYRRITSLVFWKNATKQSTE-EGGQFV
     :::::::::::::::::.:  ?:::::::::::::::::::::::::.:  :::.: .::::     :.:
     GGTVPFLARSILITSNQAPQEWYSSTAVPAVEALYRRITTLQFWKTAGEQSTEVPEGRFE
        240       250       260       270       280       290

300       310
        TLSPPCPEFPYEINY
        ...::: :::.:::
        AVDPPCALFPYKINY
        300       310
```

FIG. 3A

```
         10        20        30        40        50        60
MLLLRCCRGAAAAEVRWYYSSALLSFSAMTYPRRRYRRRRHRPRSHLGQILRRRPWLVHP
                 :           :::::::::  :::::::.:::::::.:.::
---------------W--------------PRRRYRRRRTRPRSHLGNILRRRPYLAHP
                                      10        20        30

70        80        90       100       110
--RHRYRWRRKNGIFNTRLSRTFGYTVKRTTVTTPSWAVDMMRFKIDDFVPPGGGTNKIS
 :.::::::::.::::.:::   :   :.:    . :::  :....:.:.:::.::::: .
AFRNRYRWRRKTGIFNSRLSTEFVLTIK-GGYSQPSWNVNYLKFNIGQFLPPSGGTNPLP
         40        50        60        70        80

120       130       140       150       160       170
IPFEYYRIRKVKVEFWPCSPITQGDRGVGSTAVILDDNFVTKATALTYDPYVNYSSRHTI
.:::.:::::::.:  ::.:  .:::...::::::.::::  ::::  .:  :.::::.:::::::::
LPFQYYRIRKAKYEFYPRDPITSNQRGVGSTVVILDANFVTPSTNLAYDPYINYSSRHTI
   90       100       110       120       130       140

180       190       200       210       220       230
PQPFSYHSRYFTPKPVLDSTIDYFQPNNKRNQLWLRLQTSGNVDHVGLGTAFENSKYDQD
:::.:::::::::::   ::.::: .:.:::::::::::.:    ::.:.:::  :...   :.
RQPFTYHSRYFTPKPELDQTIDWFHPNNKRNQLWLHLNTHTNVEHTGLGYALQNAATAQN
        150       160       170       180       190       200

240       250       260
YNIRVTMYVQFREFNLKDPPLEP
:  .:.:.::::::::  ::::  :.
YVVRLTIYVQFREFILKDP-LNK
        210       220       230
```

FIG. 3B

```
              10        20        30        40        50
     MKCTLVFQSRFCIFPLTFKSSASPRKFLTNVTGCCFATVTRIPLSNKVLTAVDRSLRCP-
     : ::  :::::  ::::::::::::::::::  ::: :  ::::.  :.:...:::::::::: :
—    MTCTAVFQSRCCIFPLTFKSSASPRKFLTYVTGNCSATVTKDPVSKRVLTAVDRSLRFPW
              10        20        30        40        50        60

........................................................

—    FRGAPHSISMWPSLLQYSLFCWSVPFAFSMWQRAPKYHFTLLKVCFLAKFANPWR
           70        80        90       100       110
```

*FIG. 3C*

```
              10        20        30        40        50        60
     MVTIPPLVFRWFPVCGFRVCKISSPFAFTTPRWPHNEVYIGFPITLLHFPAHFQKFSQPA
     :..:::.   .::    :. ::..:.:. :     :  .::  .:::::::.:::::::::::
     MISIPPLISTRLPVGVPRLSKITGPLALPTTGRAHYDVYSCLPITLLHLPAHFQKFSQPA
              10        20        30        40        50        60

70        80        90       100
     EIFDKRYRVLLCNGHQNPALQQGTHSSRQVTPLSLRSRSSTFNK----------------
     ::    ::: ::   .:: :  ::.:::::::::. : :  :::!..:
     EISHIRYRELLGYSHQRPRLQKGTHSSRQVAALPLVPRSSTLDKYVAFFTAVFFILLVGS
              70        80        90       100       110       120

-------------------------------------------------------------

FRFLDVAAGTKIPLHLVKSLLLSKIRKPLEVRSSTLFQTFLSANKIIKKGDWKLPYFVFL
         130       140       150       160       170       180

---------------------------

LLGRIIKGEHPPLMGLRAAFLAWHFH
         190       200
```

POSTWEANING MULTISYSTEMIC WASTING SYNDROME AND PORCINE CIRCOVIRUS FROM PIGS

CROSS-REFERENCE TO RELATED APPLICATIONS

This application is a continuation of U.S. application Ser. No. 10/653,849, filed Sep. 2, 2003, now U.S. Pat. No. 7,192,594, which is a continuation-in-part of U.S. application Ser. No. 10/334,245, filed Dec. 31, 2002, now U.S. Pat. No. 7,144,698, which is a continuation of abandoned U.S. application Ser. No. 09/935,428, filed Aug. 20, 2001, which is a continuation of abandoned U.S. application Ser. No. 09/209,961, filed Dec. 10, 1998, which claims priority to U.S. application Ser. No. 60/069,750, filed Dec. 16, 1997, and to U.S. application Ser. No. 60/069,233, filed Dec. 11, 1997.

This application is also a continuation-in-part of U.S. application Ser. No. 09/884,514, filed Jun. 19, 2001, now U.S. Pat. No. 6,660,272, which is a divisional of U.S. application Ser. No. 09/161,092, filed Sep. 25, 1998, now U.S. Pat. No. 6,391,314, which is a continuation-in-part of U.S. application Ser. No. 09/082,558, filed May 21, 1998, now U.S. Pat. No. 6,368,601, which claims priority to French Applications 97/12382, filed Oct. 3, 1997; 98/00873, filed Jan. 22, 1998 and 98/03707, filed Mar. 20, 1998.

This application is also a continuation-in-part of abandoned U.S. application Ser. No. 09/680,228, filed Oct. 6, 2000, now abandoned which is a continuation-in-part of U.S. application Ser. No. 09/583,350, filed May 31, 2000, now U.S. Pat. No. 6,517,843, which claims priority to U.S. application Ser. No. 60/151,564, filed Aug. 31, 1999.

This application is also a continuation-in-part of U.S. application Ser. No. 09/784,962, filed Feb. 16, 2001, now U.S. Pat. No. 6,953,581, which is a divisional of U.S. application Ser. No. 09/347,594, filed Jul. 1, 1999, now U.S. Pat. No. 6,217,883, which claims priority to French Application 98/08777, filed Jul. 6, 1998.

This application is related to International application Serial No. PCT/CA98/01130, filed Dec. 11, 1998.

All of the foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The present invention relates generally to viruses. More particularly, the present invention pertains to the isolation and characterization of new porcine circovirus (PCV isolates from pigs displaying postweaning multisystemic wasting syndrome (PMWS).

BACKGROUND OF THE INVENTION

Postweaning multisystemic wasting syndrome (PMWS) is a newly emerged disease of pigs. PMWS appears to destroy the host immune system and causes a high mortality rate in weaned pigs. This disease has a long incubation period, typically 3-8 weeks, and affects many organs of infected pigs. The PMWS syndrome detected in Canada, the United States and France is clinically characterized by a gradual loss of weight and by manifestations such as tachypnea, dyspnea and jaundice. From the pathological point of view, it is manifested by lymphocytic or granulomateus infiltrations, lymphadenopathies and, more rarely, by hepatitis and lymphocytic or granulomateus nephritis (Clark, Proc. Am. Assoc. Swine Prac. 1997; 499-501; La Semaine Veterinaire No. 26, supplement to La Semaine Veterinaire 1996 (834); La Semaine Veterinaire 1997 (857): 54; Gupi P. S. Nayar et al., Can. Vet. J, vol. 38, 1997; 385-387). PMWS-affected piglets often die from respiratory failure and interstitial pneumonia with histiocytic cell infiltration.

Porcine circovirus (PCV) causes worldwide infection in swine and is highly contagious. PCV was originally detected as a noncytopathic contaminant of porcine kidney (PK15) cell lines. PCV has been classified into the new virus family Circoviridae. These viruses are small, nonenveloped agents with a single-stranded circular DNA genome.

A variety of circoviruses have been identified in a range of animal species including PCV, chicken anemia virus (CAV), beak and feather disease virus (BFDV) of psittacine birds, plant viruses including subterranean clover stunt virus (SCSV), coconut foliar decay virus (CFDV) and banana bunch top virus (BBTV). There do not appear to be DNA sequence homologies or common antigenic determinants among the currently recognized circoviruses. Todd et al. (1991). Arch. Virol. 117:129-135.

Members in the circovirus family have been shown to cause anemia, immunodeficiency-related diseases and to infect macrophage cells in vitro. PCV has only recently been implicated in PMWS. See, e.g., Ellis et al. (1998). Can. Vet. J. 39:44-51 and Gopi et al. (1997) Can. Vet. J. 38:385-386. However, the etiologic association of PCV with PMWS has been questioned due to the ubiquitous presence of PCV in the pig population. Additionally, experimental infections of pigs with PCV inocula, derived from contaminated PK15 cell cultures, have failed to produce clinical disease. See, e.g., Tischer et al. (1986) Arch. Virol. 91:271-276.

Infectious agents of swine, especially viruses, not only profoundly affect the farming industry, but pose potential public health risks to humans, due to the increased interest in the use of pig organs for xenotransplantation in humans. Previous diagnosis of PMWS disease has been based on histopathological examination. Accordingly, there is a need for improved methods of diagnosing the presence of PMWS-associated pathogens, as well as for preventing PMWS disease.

SUMMARY OF THE INVENTION

The present invention is based on the discovery of a new virus, designated "PCV Type II" or "PCVII" herein, isolated from homogenized tissues of PMWS-affected piglets. Characterization of the virus shows that it shares common features with the nonpathogenic porcine circovirus obtained from persistently infected PK15 cells, designated "PCV Type I" or "PCVI" herein. The entire DNA genome of a novel PCV variant, PCVII 412, as well as several additional PCVII isolates, have been cloned and sequenced. Portions of these DNA sequences are useful as probes to diagnose the presence of virus in clinical samples, and to isolate other naturally occurring variants of the virus. An understanding of the genomic sequence of PCVII also makes available the polypeptide sequences of the various proteins encoded within the open reading frames of the viral genome and permits production of these peptides or portions thereof which are useful as standards or reagents in diagnostic tests and as components of vaccines. Protective antibodies may also be raised from the proteins and may be produced in polyclonal or monoclonal form.

The availability of the entire PCVII sequence thus permits the design and construction of polypeptides which may either serve as vaccines or diagnostic reagents, or as intermediates in the production of monoclonal antibody (Mab) preparations useful in passive immunotherapy against PMWS, or as intermediates in the production of antibodies useful as diagnostic reagents.

Accordingly, in one aspect, the invention relates to polynucleotides useful for the production of PCVII diagnostics and vaccines derived from the PCVII genome. In one particular embodiment, the polynucleotides are capable of selectively hybridizing to a PCVII nucleotide sequence and comprise at least about 8 contiguous nucleotides derived from, or complementary to, a PCVII sequence depicted in FIGS. 4A-4C (SEQ ID NO:1, SEQ ID NO:11 and SEQ ID NO: 12). In another embodiment, the polynucleotide encodes an immunogenic PCVII polypeptide having at least about 85% identity to a polypeptide selected from the group consisting of a polypeptide derived from (a) open reading frame (ORF) 1 (SEQ ID NO:3), (b) ORF 2 (SEQ ID NO:9), (c) ORF 3 (SEQ ID NO:7), (d) ORF 4 (SEQ ID NO:20), (e) ORF 5 (SEQ ID NO:21), (f) ORF 6 (SEQ ID NO:5), and (g) immunogenic fragments of (a)-(f) comprising at least about 5 amino acids. In a particularly preferred embodiment, the polynucleotide encodes the polypeptide of ORF 6 (SEQ ID NO:5), or immunogenic fragments thereof.

The invention thus relates to utilizing these polynucleotide sequences or portions thereof as oligomeric probes, for production of peptides which can serve as diagnostic reagents or as vaccine antigens, to the peptides themselves, and to polyclonal and monoclonal antibodies useful in diagnosis and treatment of the disease.

Other aspects of the invention include expression systems which are capable of effecting the production of a desired protein encoded by sequences derived from the complete genome, to recombinant vectors containing such systems or portions thereof, to recombinant host cells transformed with such vectors, to proteins produced by the transformed cells, and to vaccines prepared from such proteins. In addition, the invention relates to peptide sequences representing epitopes encoded by the genome, and to such sequences covalently linked to label or to carrier proteins. Also encompassed by the present invention are the various ORFs of the PCVII genome, as well as the proteins encoded by these ORFs, and portions thereof.

The invention also relates to the methods of preparing polypeptide compositions, such as vaccines and immunodiagnostic compositions, and immunoglobulins, and to immunoassays and kits for assays containing the primers, probes, polypeptides, and/or immunoglobulins. In one embodiment, then, the invention pertains to a method of detecting PCVII antibodies in a biological sample comprising:

(a) providing a biological sample;

(b) reacting the biological sample with an immunogenic PCVII polypeptide as described above, under conditions which allow PCVII antibodies, when present in the biological sample, to bind to the PCVII polypeptide to form an antibody/antigen complex; and (c) detecting the presence or absence of the complex, thereby detecting the presence or absence of PCVII antibodies in the sample.

In another embodiment, the invention is directed to a nucleic acid hybridization assay for detecting PCVII homologous sequences in a biological sample comprising:

(a) incubating the biological sample with a polynucleotide according to claim 1 under conditions which promote the formation of nucleic acid complexes between the polynucleotide and PCVII nucleic acid present in the biological sample; and (b) detecting the complexes containing the polynucleotide.

These and other aspects and features of the invention will be more fully appreciated when the following detailed description of the invention is read in conjunction with the accompanying figures.

BRIEF DESCRIPTION OF THE DRAWINGS

The following Detailed Description, given by way of example, but not intended to limit the, invention to specific embodiments described, may be understood in conjunction with the accompanying drawings, incorporated herein by reference, in which:

FIGS. 2A-2C show the nucleotide sequence for the PCVII 412 genome (SEQ ID NO:1). Both senses are shown. The amino acid sequences corresponding to the translation products of the various ORFs are also shown as indicated: ORF 1 (SEQ. ID NO:3); ORF 2 (SEQ ID NO:9); ORF 3 (SEQ ID NO:7); ORF 4 (SEQ ID NO:20); ORF 5 (SEQ ID NO:21); and ORF 6 (SEQ ID NO:5).

FIGS. 3A-3D show comparisons of amino acid sequences from open reading frames of PCVII 412, versus corresponding open reading frames of PCVI isolated from PK15 cells. FIG. 3A shows the amino acid sequence of ORF 1 of PCVII 412 (top line, SEQ ID NO:3) compared to the corresponding ORF from PCVI (bottom line, SEQ ID NO:4). FIG. 3B shows the amino acid sequence of ORF 6 of PCVII 412 (top line, SEQ ID NO:S) compared to the corresponding ORF from PCVI (bottom line, SEQ ID NO:6). FIG. 3C shows the amino acid sequence of ORF 3 of PCVII 412 (top line, SEQ ID NO:7) compared to the corresponding ORF from PCVI (bottom line, SEQ ID NO:8). FIG. 3D shows the amino acid sequence of ORF 2 of PCVII 412 (top line, SEQ ID NO:9) compared to the corresponding ORF from PCVI (bottom line, SEQ ID NO:10).

FIGS. 4A-4B show comparisons of the nucleotide sequences of various PCV isolates: PCVI from PK15 cells (SEQ ID NO:2), PCVII 412 (SEQ ID NO:1), PCVII 9741 (SEQ ID NO:11) and PCVII B9 (SEQ ID NO: 12).

DETAILED DESCRIPTION OF THE INVENTION

Figure 1:
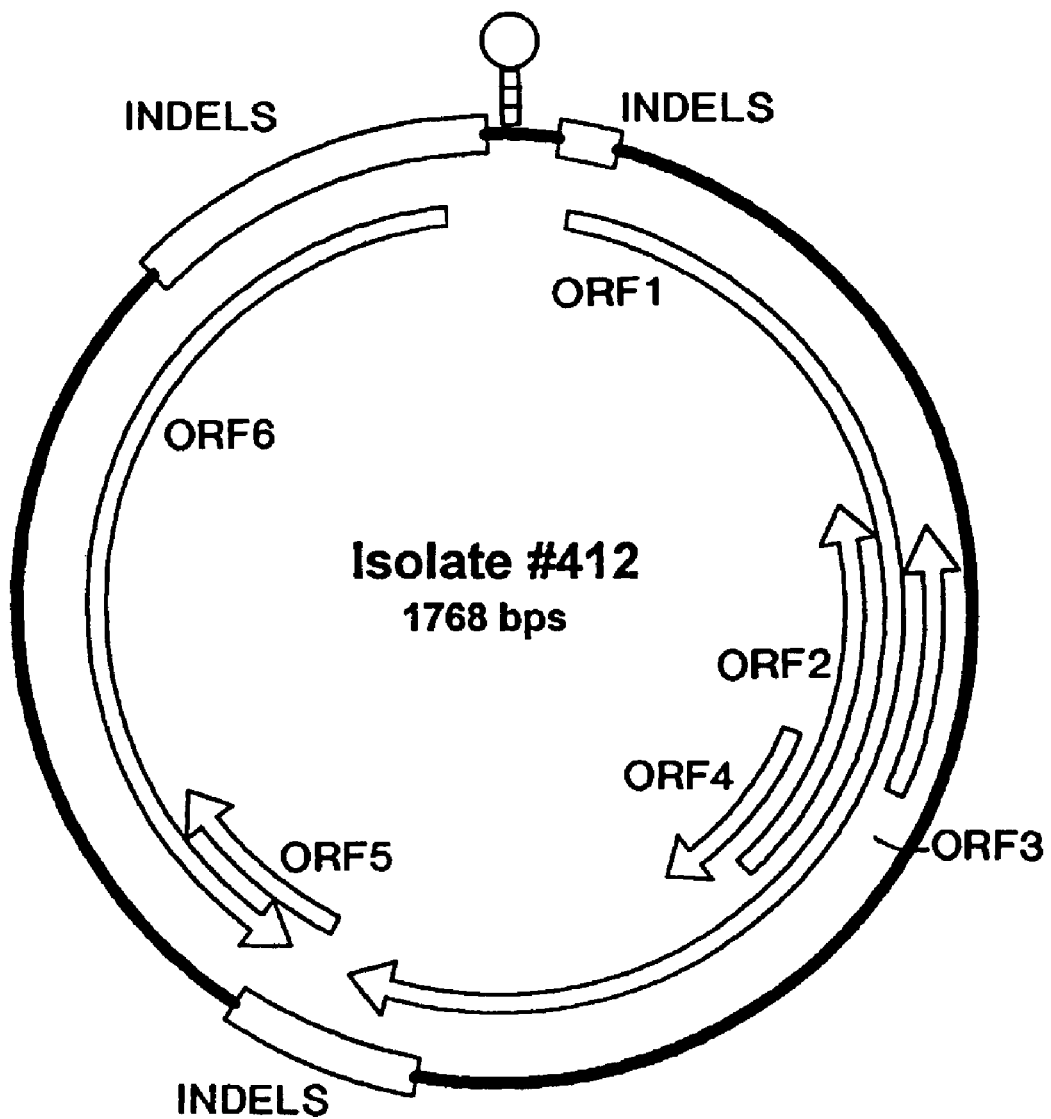
FIG. 1 shows a diagram of PCVII 412, showing the location of the open reading frames.
Figure 5:
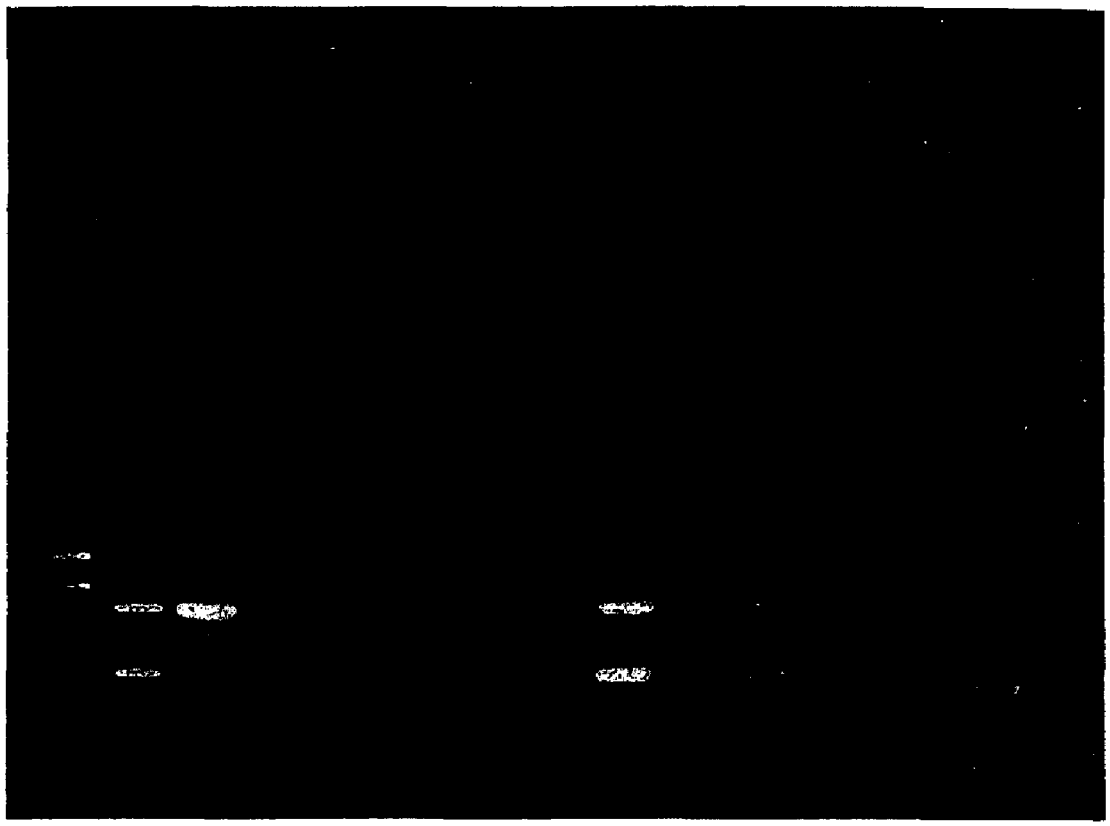
FIG. 5 shows the results of multiplex PCR used for the detection of PCV infection. The assay both identified PCV infection and distinguished between the presence of PCVI and PCVI. Lane 1 is a molecular weight marker. Lanes 2-4 are controls in the order of PCVII, PCVI and negative. Lanes 5-13 are blood samples collected from piglets from a PMWS-affected herd.
Figure 6:
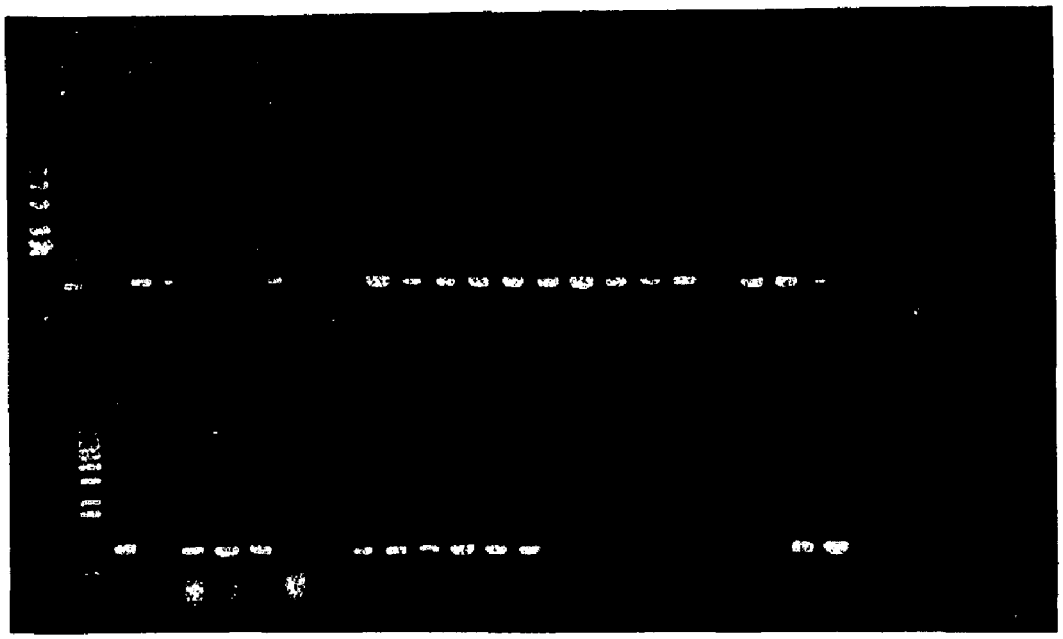
FIG. 6 shows the results of multiplex PCR conducted on various tissue samples from a PMWS-affected piglet. Lane 1 in both rows is a molecular weight marker. Lane 2 in the top row is a positive PCVII control while lane 3 is a negative control. The remaining lanes are various tissue samples collected from the PMWS-affected piglet.

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook, Fritsch & Maniatis, *Molecular Cloning: A Laboratory Manual*, Vols. I, II and III, Second Edition (1989); DNA Cloning, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (WL press, 1986); Perbal, B., *A Practical Guide to Molecular Cloning* (1984), the series, *Methods In Enzymology* (S. Colowick and N Kaplan eds., Academic Press, Inc.); and *Handbook of Experimental Immunology*, Vols. I-IV (D. M. Weir and C. C. Blackwell eds., 1986, Blackwell Scientific Publications).

Before describing the present invention in detail, it is to be understood that this invention is hot limited to particular DNA, polypeptide sequences or process parameters as such may, of course, vary. It is also to be understood that the terminology used herein is for the purpose of describing particular embodiments of the invention only, and is not intended to be limiting.

It must be noted that, as used in this specification and the appended claims, the singular forms "a", "an" and "the" include plural referents unless the content clearly dictates otherwise. Thus, for example, reference to "an antigen" includes a mixture of two or more antigens, reference to "an excipient" includes mixtures of two or more excipients, and the like.

The following amino acid abbreviations are used throughout the text:

Alanine: Ala (A)
Asparagine: Asn (N)
Cysteine: Cys (C)
Glutanuic acid: Glu (E)
Histidine: His (H)
Leucine: Leu (L)
Methionine: Met (M)
Proline: Pro (P)
Threonine: Thr (T)
Tyrosine: Tyr (Y)
Arginine: Arg (R)
Aspartic acid: Asp (D)
Glutamnine: Gln (Q)
Glycine: Gly (G)
Isoleucine: Ile (I)
Lysine: Lys (K)
Phenylalanine: Phe (F)
Serine: Ser (S)
Tryptophan: Trp (W)
Valine: Val (V)

A. Definitions

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed, and are intended to be defined as indicated below.

Figure 4A:
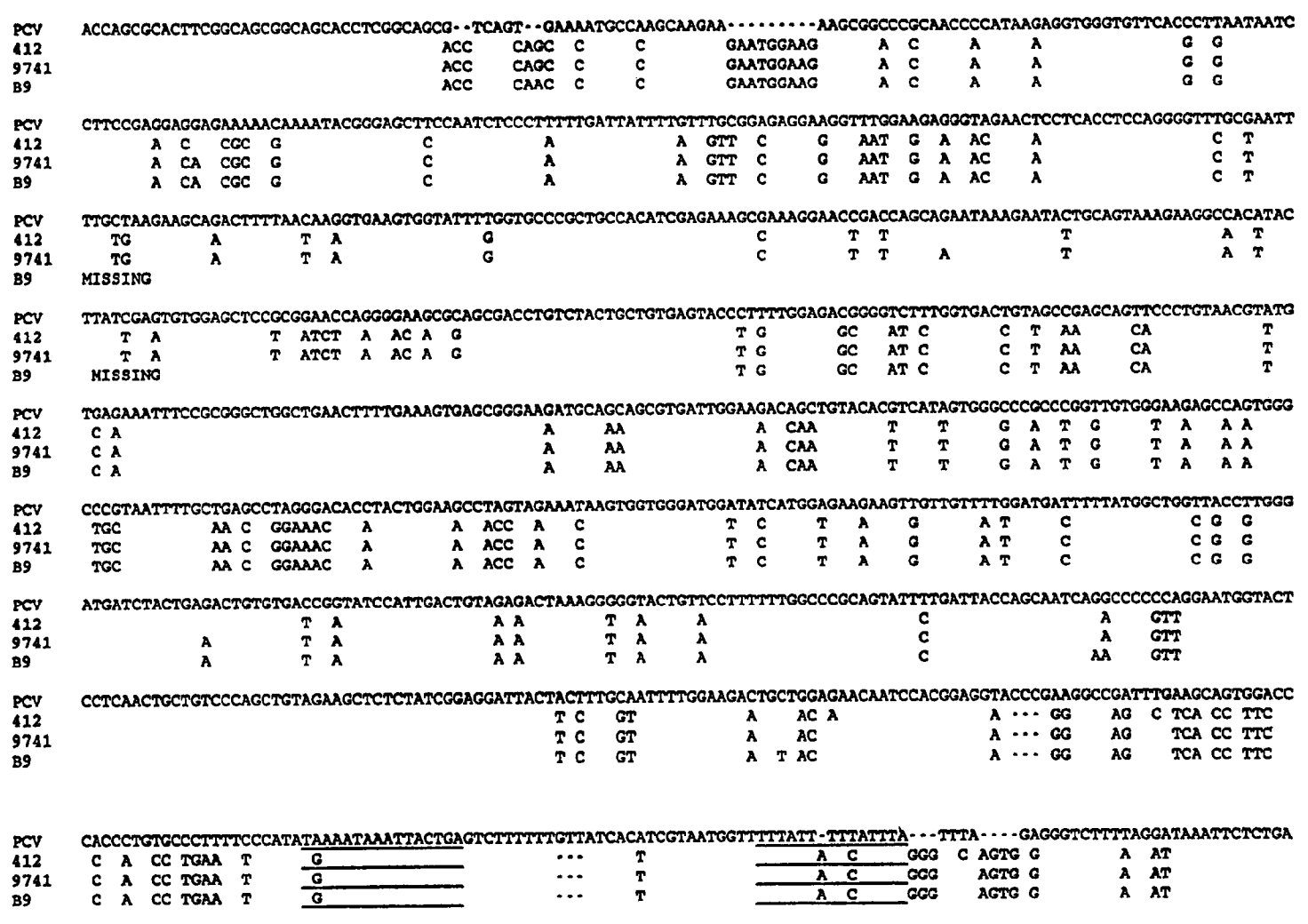
Figure 4B:
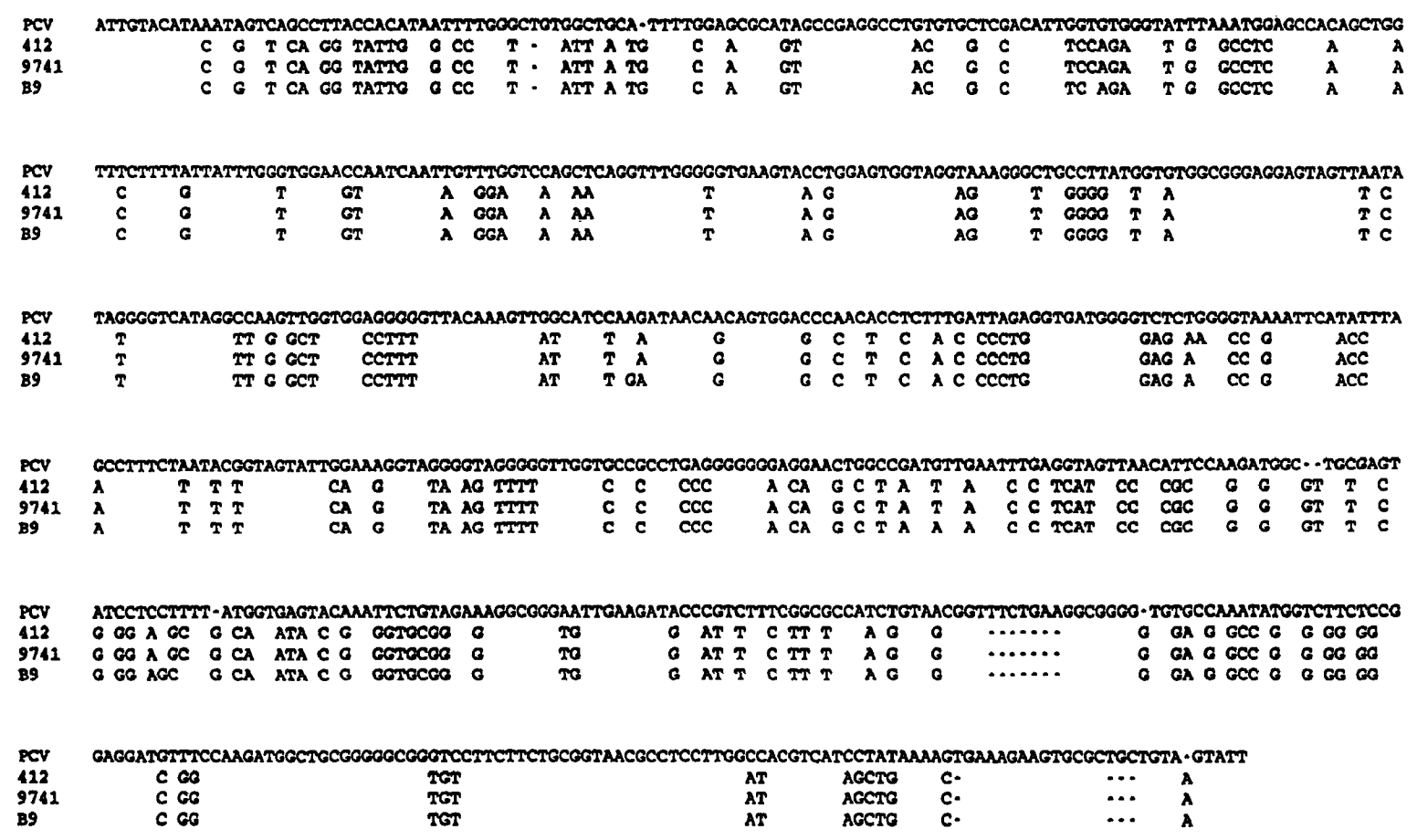

The terms "PCVII protein," "PMWS protein" or a nucleotide sequence encoding the same, intend a protein or a nucleotide sequence, respectively, which is derived from a novel PCVII isolate, as described herein. The nucleotide sequences of several PCVII isolates are shown in FIGS. 4A-4B and the amino acid sequences corresponding to the six identified PCVII ORFs are shown in FIGS. 2A-2C. However, a PCVII or PMWS protein, or a gene encoding the same, as defined herein is not limited to the depicted sequence.

Further, as used herein, a nucleotide sequence "derived from" a PCVII genome or its complement refers to a sequence which retains the essential properties of the illustrated polynucleotide, representing a portion of the entire sequence from which it is derived, for the purpose intended. A specific, but nonlimiting, example of such derivation is represented by a sequence which encodes an identical or substantially identical amino acid sequence, but, because of codon degeneracy, utilizes different specific codons; another example is a sequence complementary to the viral DNA. A probe or oligonucleotide useful in diagnostic tests needs to retain the complementarity of the sequence shown but may be shorter than the entire sequence or may skip over portions of it. However, for use in manipulation or expression, nucleotide changes are often desirable to create or delete restriction sites, provide processing sites, or to alter the encoded amino acid sequence in ways which do not adversely affect functionality. The terms "nucleotide sequence" and "polynucleotide" refer both to ribonucleotide and a deoxyribonucleotide sequences and include both the genomic strand and its complementary sequence.

A sequence "derived from" the nucleotide sequence which comprises the genome of a PCVII isolate therefore refers to a sequence which is comprised of a sequence corresponding to a region of the genomic nucleotide sequence (or its complement), or a combination of regions of that sequence modified in ways known in the art to be consistent with its intended use. These sequences are, of course, not necessarily physically derived from the nucleotide sequence of the gene, but refer to polynucleotides generated in whatever manner which are based on the information provided by the sequence of bases in the region(s) from which the polynucleotide is derived. For example, regions from which typical DNA sequences can be "derived" include regions encoding specific epitopes. Similarly, a peptide "derived from" a PCVII ORF refers to an amino acid sequence substantially identical to that of these polypeptides or a portion thereof, having the same biological properties as that portion.

Furthermore, the derived protein or nucleotide sequences need not be physically derived from the genes described above, but may be generated in any manner, including for example, chemical synthesis, isolation (e.g., from a PCVII isolate) or by recombinant production, based on the information provided herein. Additionally, the term intends proteins having amino acid sequences substantially homologous (as defined below) to contiguous amino acid sequences encoded by the genes, which display immunological activity.

Thus, the terms intend full-length, as well as immunogenic, truncated and partial sequences, and active analogs and precursor forms of the proteins. Also included in the term are nucleotide fragments of the particular gene that include at least about 8 contiguous base pairs, more preferably at least about 10-20 contiguous base pairs, and even at least about 25 to 50 or 75 or more contiguous base pairs of the gene. Such fragments are useful as probes, in diagnostic methods, and for the recombinant production of proteins, as discussed more fully below.

The terms also include proteins in neutral form or in the form of basic or acid addition salts depending on the mode of preparation. Such acid addition salts may involve free amino groups and basic salts may be formed with free carboxyls. Pharmaceutically acceptable basic and acid addition salts are discussed further below. In addition, the proteins may be modified by combination with other biological materials such as lipids and saccharides, or by side chain modification, such as acetylation of amino groups, phosphorylation of hydroxyl side chains, oxidation of sulfhydryl groups, glycosylation of amino acid residues, as well as other modifications of the encoded primary sequence.

The term therefore intends deletions, additions and substitutions to the sequence, so long as the polypeptide functions to produce an immunological response as defined herein. In this regard, particularly preferred substitutions will generally be conservative in nature, i.e., those substitutions that take place within a family of amino acids. For example, amino acids are generally divided into four families: (1) acidic—aspartate and glutamate; (2) basic-lysine, arginine, histidine; (3) non-polar—alanine, va line, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. For ex ample, it is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule, but possessing minor amino acid substitutions that do not substantially affect the immunogenicity of the protein, are therefore within the definition of the reference polypeptide.

An "open reading frame" or "ORF" is a region of a polynucleotide sequence which encodes a polypeptide.

By "postweaning multisystemic wasting syndrome" or "PMWS" is meant a disease of vertebrate animals, in particular pigs, which is characterized clinically by progressive weight loss, tachypnea, dyspnea and jaundice. Consistent pathologic changes include lymphocytic to granulomatous interstitial pneumonia, lymphadenopathy, and, less frequently, lymphocytic to granulomatous hepatitis and nephritis. See, e.g., Clark, E. G. *Proc. Am. Assoc. Swine Pract.* 1997:499-501; and Harding, J. *Proc. Am. Assoc. Swine Pract.* 1997:503.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

The term "vaccine composition" intends any pharmaceutical composition containing an antigen, which composition can be used to prevent or treat a disease or condition in a subject. The term thus encompasses both subunit vaccines, as described below, as well as compositions containing whole killed, attenuated or inactivated microbes.

By "subunit vaccine composition" is meant a composition containing at least one immunogenic polypeptide, but not all antigens, derived from or homologous to an antigen from a pathogen of interest. Such a composition is substantially free of intact pathogen cells or particles, or the lysate of such cells or particles. Thus, a "subunit vaccine composition" is prepared from at least partially purified (preferably substantially purified) immunogenic polypeptides from the pathogen, or recombinant analogs thereof. A subunit vaccine composition can comprise the subunit antigen or antigens of interest substantially free of other antigens or polypeptides from the pathogen.

The compositions of the invention can include any pharmaceutically acceptable carrier known in the art.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to the composition or vaccine of interest. Usually, an "immunological response" includes but is not limited to one or more of the following effects: the production of antibodies, B cells, helper T cells, suppressor-T cells; and/or cytotoxic T cells and/or $\gamma\delta$ T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The terms "immunogenic" protein or polypeptide refer to an amino acid sequence which elicits an immunological response as described above. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

Synthetic antigens are also included within the definition, for example, polyepitopes, flanking epitopes, and other recombinant or synthetically derived antigens. See, e.g., Bergmann et al. (1993) *Eur. J. Immunol* 23:2777-2781; Bergmann et al. (1996) *J. Immunol.* 157:3242-3249, Suhrbier, A. (1997) *Immunol and Cell Biol.* 75:402-408; Gardner et al. (1998) 12th World AIDS Conference, Geneva, Switzerland, Jun. 28-Jul. 3, 1998.

Immunogenic fragments, for purposes of the present invention, will usually include at least about 3 amino acids, preferably at least about 5 amino acids, more preferably at least about 10-15 amino acids, and most preferably 25 or more amino acids, of the molecule. There is no critical upper limit to the length of the fragment, which could comprise nearly the full-length of the protein sequence, or even a fusion protein comprising two or more epitopes of the protein.

Any of the above immunogenic proteins, immunogenic polypeptides, synthetic antigens, or immunogenic fragments can be used to raise antibodies in a host.

"Native" proteins or polypeptides refer to proteins or polypeptides isolated from the source in which the proteins naturally occur. "Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "vector" is a replicon, such as a plasmid, phage, or cosmid, to which another DNA segment may be attached so as to bring about the replication of the attached segment.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

DNA "control elements" refers collectively to promoters, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered. "operably linked" to the coding sequence.

A control element, such as a promoter, "directs the transcription" of a coding sequence in a cell when RNA polymerase will bind the promoter and transcribe the coding sequence into mRNA, which is then translated into the polypeptide encoded by the coding sequence.

A "host cell" is a cell which has been transformed, or is capable of transformation, by an exogenous nucleic acid molecule.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

"Homology" refers to, the percent identity between two polynucleotide or two polypeptide moieties. Two DNA, or two polypeptide sequences are "substantially homologous" to each other when the sequences exhibit at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman (1981) *Advances in Appl. Math.* 2:482-489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

Two nucleic acid fragments are considered to be "selectively hybridizable" to a PCVII polynucleotide, if they are capable of specifically hybridizing to a PCVII nucleic acid or a variant thereof (e.g., a probe that hybridizes to a PCVII nucleic acid but not to polynucleotides from other members of the circovirus family) or specifically priming a polymerase chain reaction: (i) under typical hybridization and wash conditions, as described, for example, in Sambrook et al., supra and Nucleic Acid Hybridization, supra, (ii) using reduced stringency wash conditions that allow at most about 25-30% basepair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each, or (iii) selecting primers for use in typical polymerase chain reactions (PCR) under standard conditions (described for example, in Saiki et al. (1988) *Science* 239:487-491), which result in specific amplification of sequences of PCVII or its variants.

The term "functionally equivalent" intends that the amino acid sequence of a protein is one that will elicit a substantially equivalent or enhanced immunological response, as defined above, as compared to the response elicited by a reference amino acid sequence, or an immunogenic portion thereof.

A "heterologous" region of a DNA construct is an identifiable segment of DNA within or attached to another DNA molecule that is not found in association with the other molecule in nature. Thus, when the heterologous region encodes a viral gene, the gene will usually be flanked by DNA that does not flank the viral gene in the genome of the source virus. Another example of the heterologgus coding sequence is a construct where the coding sequence itself is not found in nature (e.g., synthetic sequences having codons different from the native gene). Allelic variation or naturally occurring mutational events do not give rise to a heterologous region of DNA, as used herein.

The term "treatment" as used herein refers to either (i) the prevention of infection or reinfection (prophylaxis), or (ii) the reduction or elimination of symptoms of the disease of interest (therapy).

As used herein, a "biological sample" refers to a sample of tissue or fluid isolated from a subject, including but not limited to, for example, blood, plasma, serum, fecal matter, urine, bone marrow, bile, spinal fluid, lymph tissue and lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used under the invention include fluorescein, rhodamine, dansyl, umbelliferone, Texas red, luminol, NADPH and α-β.-galactosidase.

By "vertebrate subject" is meant any member of the subphylum cordata, including, without limitation, mammals such as cattle, sheep, pigs; goats, horses, and man; domestic animals such as dogs and cats; and birds, including domestic, wild and game birds such as cocks and hens including chickens, turkeys and other gallinaceous birds. The term does not denote a particular age. Thus, adult and newborn animals, as well as fetuses, are intended to be covered.

B. General Methods

Central to the present invention is the discovery of a new circovirus termed "PCVII" herein, isolated from PMWS-affected pigs. The useful materials and processes of the present invention are made possible by the discovery of a family of nucleotide sequences, each containing an entire genome of a novel PCVII virus. The availability of this family of polynucleotides, first, permits the isolation of other members of the genome family which differ by small heterogeneities. Second, it permits the construction of DNA fragments and proteins useful in diagnosis. For example, oligomers of at least about 8-10 nucleotides or more, preferably, oligomers comprising at least about 15-20 nucleotides, are useful as hybridization probes in disease diagnosis. Such probes may be used to detect the presence of the viral genome in, for example, sera of subjects suspected of harboring the virus. Similarly, the genes encoding the proteins can be cloned and used to design probes to detect and isolate homologous genes in other viral isolates.

The PCVII sequences also allow the design and production of PCVII-specific polypeptides which are useful as diagnostic reagents for the presence of antibodies raised against PCVII in serum or blood. Antibodies against these polypeptides are also useful as diagnostics. Because several open reading frames can be deciphered in the context of the complete genome, the primary structures of PCVII-related proteins can be deduced. Finally, knowledge of the gene sequences also enables the design and production of vaccines effective against PCVII and hence useful for the prevention of PMWS and also for the production of protective antibodies.

Sequencing information available from the genome allows the amino acid sequence of the various polypeptides encoded by the viral genome to be deduced and suitable epitopes identified. The full-length proteins encoded by the several ORFs identified in the PCVII genome, or suitable portions thereof, can be produced using fragments of the relevant DNA which are obtained and expressed independently, thus providing desired polypeptides using recombinant techniques. Both procaryotic and eucaryotic hosts are useful for such expression. Short polypeptide fragments may also be chemically synthesized and linked to carrier proteins for use as vaccines. In addition, epitopes may be produced linked to a protein conferring immunogenicity. The proteins thus produced may themselves be used as vaccines, or may be used to induce immunocompetent B cells in hosts, which B cells can then be used to produce hybridomas that secrete antibodies useful in passive immunotherapy.

More particularly, the complete genetic sequences for three isolates of PCVII, PCVII 412 (SEQ ID NO:1), PCVII 9741 (SEQ ID NO:11), AND PCVII B9 (SEQ ID NO:12), are shown in FIGS. 4A-4B. The percent nucleotide sequence homologies among the various isolates of PCVII are more than 99% identical. The newly discovered viral genome shares approximately 76% identity with PCV isolated from infected PK15 cells at the nucleotide level (termed "PCVI" herein). As described further in the examples, nucleotide insertions and deletions (indels) have been found in three regions.

As shown in FIG. 1, the new virus contains at least six potential open reading frames (ORFs) encoding proteins comprising more than 50 amino acid residues, while PCVI derived from PK15 has seven potential ORFs. The ORFs for representative PCVII isolates occur at the following nucleotide positions, using the numbering of the PCVII isolates shown in FIGS. 4A-4B:

| ORF 1 | 51 to 992   |
| ORF 2 | 671 to 360  |
| ORF 3 | 565 to 389  |
| ORF 4 | 553 to 729  |
| ORF 5 | 1016 to 1174 |
| ORF 6 | 1735 to 1037 |

The polypeptides encoded by the six ORFs are shown in FIGS. 2A-2C.

The main cellular targets for PCVII are mononuclear cells in the peripheral blood, likely macrophage cells, although the virus is also found in various tissues and organs in infected animals. The affected macrophages lose their normal function, causing damage to the host immune system, leading to death.

The cloning and sequencing of the novel circoviruses has provided information about the causative agent of PMWS. As explained above, the sequencing information, as well as the clones and its gene products, are useful for diagnosis and in vaccine development. In particular, PCR and antibody-based diagnostic methods are useful in the diagnosis of the disease and were used herein to specifically identify and differentiate this novel PCVII virus from PCVI derived from persistently infected PK15 cells. The sequencing information is also useful in the design of specific primers, to express viral-specific gene products, to study the viral structure, to generate specific antibodies and to identify virulent genes in porcine circovirus-related diseases.

B.1. Preparation of the PCVII Gene Sequence

The new viral genomes of PCVII were obtained from viruses isolated from tissue of PMWS-affected pigs. Viral DNA was extracted from variable sources, including pellets of infected Dulac and Vero cells, peripheral blood buffy-coat cells, tissues from infected animals and serum. DNA was extracted from the samples using techniques discussed more fully in the examples.

By comparing the sequence and structural similarity among the known viruses in the circovirus family, a unique primer was designed taking advantage of the complementary sequences of a conserved stem loop structure. One-primer PCR was then performed and the products cloned. Two full-length viral genomes in different orientations inserted into a plasmid vector were completely sequenced in both directions. Additional PCR products were made and sequenced to ensure the fidelity of the primer/stem loop region.

Using similar primers, other PCVII isolates, including PCVII 9741, and PCVII B9, were obtained. This appears to be the first time a circovirus has been cloned from viral particles instead of from a replicated form of DNA. The description of the method to retrieve the PCVII genome is, of course, mostly of historical interest. The resultant sequence is provided herein, and the entire sequence, or any portion thereof, could also be prepared using synthetic methods, or by a combination of synthetic methods with retrieval of partial sequences using methods similar to those here described.

B.2. Production of PCVII Proteins

The availability of PCVII genomic sequences permits construction of expression vectors encoding viral polypeptides and antigenically active regions thereof, derived from the PCVII genome. Fragments encoding the desired proteins can be obtained from cDNA clones using conventional restriction digestion or by synthetic methods and are ligated into vectors, for example, containing portions of fusion sequences such as β-galactosidase. Any desired portion of the PCVII genome containing an open reading frame can be obtained as a recombinant protein, such as a mature or fusion protein, or can be provided by chemical synthesis or general recombinant means.

It is readily apparent that PCVII proteins encoded by the above-described DNA sequences, active fragments, analogs and chimeric proteins derived from the same, can be produced by a variety of methods. Recombinant products can take the form of partial protein sequences, full-length sequences, precursor forms that include signal sequences, mature forms without signals, or even fusion proteins (e.g., with an appropriate leader for the recombinant host, or with another subunit antigen sequence for another pathogen).

Gene libraries can be constructed and the resulting clones used to transform an appropriate host cell. Colonies can be pooled and screened using polyclonal serum or monoclonal antibodies to the PCVII protein.

Alternatively, once the amino acid sequences are determined, oligonucleotide probes which contain the codons for a portion of the determined amino acid sequences can be prepared and used to screen genomic or cDNA libraries for genes encoding the subject proteins. The basic strategies for preparing oligonucleotide probes and DNA libraries, as well as their screening by nucleic acid hybridization, are well known to those of ordinary skill in the art. See, e.g., DNA Cloning: Vol. I, supra; Nucleic Acid Hybridization, supra; Oligonucleotide Synthesis, supra; Sambrook et al., supra. Once a clone from the screened library has been identified by positive hybridization, it can be confirmed by restriction enzyme analysis and DNA sequencing that the particular library insert contains a PCVII protein gene or a homolog thereof. The genes can then be further isolated using standard techniques and, if desired, PCR approaches or restriction enzymes employed to delete portions of the full-length sequence.

Similarly, genes can be isolated directly from viruses using known techniques, such as phenol extraction and the sequence further manipulated to produce any desired alterations. See, e.g., the examples herein and Hamel et al. (1998) *J. Virol.* 72:5262-5267, for a description of techniques used to obtain and isolate viral DNA.

Alternatively, DNA sequences can be prepared synthetically rather than cloned. The DNA sequences can be designed with the appropriate codons for the particular amino acid sequence if the sequences are to be used in protein production. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV.14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, Sambrook et al., supra; DNA Cloning, supra; B. Perbal, supra.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. If a signal sequence is included, it can either be the native, homologous sequence, or a heterologous sequence. Leader sequences can be removed by the host in post-translational processing. See, e.g., U.S. Pat. Nos. 4,431,739; 4,425,437; 4,338,397.

Other regulatory sequences may also be desirable which allow for regulation of expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the desired PCVII protein. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are described in, e.g., Sambrook et al., supra; DNA Cloning, supra; Nucleic Acid Hybridization, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maitosa, Hansenula polymorpha, Kluyveromyces fragilis, Kluyveromyces lactis, Pichia guilerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Depending on the expression system and host selected, the proteins of the present invention are produced by culturing host cells transformed by an expression vector described above under conditions whereby the protein of interest is expressed. The protein is then isolated from the host cells and purified. If the expression system secretes the protein into the growth media, the protein can be purified directly from the media. If the protein is not secreted, it is isolated from cell lysates. The selection of the appropriate growth conditions and recovery methods are within the skill of the art.

The proteins of the present invention may also be produced by chemical synthesis such as solid phase peptide synthesis, using known amino acid sequences or amino acid sequences derived from the DNA sequence of the genes of interest. Such methods are known to those skilled in the art. See, e.g., J. M. Stewart and J. D. Young, *Solid Phase Peptide Synthesis*, 2nd Ed., Pierce Chemical Co., Rockford, Ill. (1984) and G. Barany and R. B.; Merrifield, *The Peptides: Analysis, Synthesis, Biology*, editors E. Gross and J. Meienhofer, Vol. 2, Academic Press, New York, (1980), pp. 3-254, for solid phase peptide synthesis techniques; and M Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis. Chemical synthesis of peptides may be preferable if a small fragment of the antigen in question is capable of raising an immunological response in the subject of interest.

Analysis of the genome shows the presence of at least six open reading frames, at least one of which encodes the putative DNA replicase gene.

B.3. Preparation of Antigenic Polypeptides and Conjugation with Carrier

The antigenic region of peptides is generally relatively small—typically 10 amino acids or less in length. Fragments of as few as 5 amino acids may typically characterize an antigenic region. Accordingly, using the genome of PCVII as a basis, DNAs encoding short segments of polypeptides, derived from any of the various ORFs of PCVII, such as ORFs 1-6, and particularly ORF 6, can be expressed recombinantly either as fusion proteins or as isolated peptides. In addition, short amino acid sequences can be chemically synthesized. In instances wherein the synthesized peptide is correctly configured so as to provide the correct epitope, but too small to be immunogenic, the peptide may be linked to a suitable carrier.

A number of techniques for obtaining such linkage are known in the art, including the formation of disulfide linkages using N-succinimidyl-3-(2-pyridyl-thio)propionate (SPDP) and succinimidyl 4-(N-maleimido-methyl)cyclohexane-1-carboxylate (SMCC) obtained from Pierce Company, Rockford, Ill. (If the peptide lacks a sulfhydryl, this can be provided by addition of a cysteine residue.) These reagents create a disulfide linkage between themselves and peptide cysteine residues on one protein and an amide linkage through the e-amino on a lysine, or other free amino group in the other. A variety of such disulfide/amide-forming agents are known. See, for example, *Immun. Rev.* (1982) 62:185. Other bifunctional coupling agents form a thioether rather than a disulfide linkage. Many of these thioether-forming agents are commercially available and include reactive esters of 6-maleimidocaproic acid, 2-bromoacetic acid, 2-iodoacetic acid, 4-(N-maleimido-methyl)cycloh-exane-1-carboxylic acid, and the like. The carboxyl groups can be activated by combining them with succinimide or 1-hydroxy-2-nitro-4-sulfo nic acid, sodium salt. The foregoing list is not meant to exhaustive, and modifications of the named compounds can clearly be used. Any carrier may be used, which does not itself induce the production of antibodies harmful to the host, such as the various serum albumins, tetanus toxoids, or keyhole limpet hemocyanin (KLH).

The conjugates, when injected into suitable subjects, will result in the production of antisera which contain immunoglobulins specifically reactive against not only the conjugates, but also against fusion proteins carrying the analogous portions of the sequence, and against appropriate determinants within whole PCVII.

B.4. Production of Antibodies

Proteins encoded by the novel viruses of the present invention, or their fragments, can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. See, e.g., Jurgens et al. (1985) *J. Chrom.* 348: 363-370. If serum containing polyclonal antibodies is used, the polyclonal antibodies can be purified by immunoaffinity chromatography, using known procedures.

Monoclonal antibodies to the proteins and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibod-* ies and T-cell Hybridomas (1981); Kennett et al., Monoclonal Antibodies (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the desired protein, or fragment thereof, can be screened for various properties; i.e., for isotype, epitope, affinity, etc. Monoclonal antibodies are useful in purification, using immunoaffinity techniques, of the individual antigens which they are directed against. Both polyclonal and monoclonal antibodies can also be used for passive immunization or can be combined with subunit vaccine preparations to enhance the immune response. Polyclonal and monoclonal antibodies are also useful for diagnostic purposes.

B.5. Vaccine Formulations and Administration

The novel viral proteins of the present invention can be formulated into vaccine compositions, either alone or in combination with other antigens, for use in immunizing subjects as described below. Methods of preparing such formulations are described in, e.g., Remington's Pharmaceutical Sciences, Mack Publishing Company, Easton, Pa., 18 Edition, 1990. Typically, the vaccines of the present invention are prepared as injectables, either as liquid solutions or suspensions. Solid forms suitable for solution in or suspension in; liquid vehicles prior to injection may also be prepared. The preparation may also be emulsified or the active ingredient encapsulated in liposome vehicles. The active immunogenic ingredient is generally mixed with a compatible pharmaceutical vehicle, such as, for example, water, saline, dextrose, glycerol, ethanol, or the like, and combinations thereof. In addition, if desired, the vehicle may contain minor amounts of auxiliary substances such as wetting or emulsifying agents and pH buffering agents.

Adjuvants which enhance the effectiveness of the vaccine may also be added to the formulation. Such adjuvants include, without limitation, adjuvants formed from aluminum salts (alum), such as aluminum hydroxide, aluminum phosphate, aluminum sulfate, etc; oil-in-water and water-in-oil emulsion formulations, such as Complete Freunds Adjuvant (CFA), Incomplete Freunds Adjuvant (IFA), pyridine and dimethyldioctadecyl ammonium bromide (DDA); adjuvants formed from bacterial cell wall components such as adjuvants including monophosphoryl lipid A (APL) (Imoto et al. (1985) Tet. Lett. 26:1545-1548), trehalose dimycolate (TDM), and cell wall skeleton (CWS); adjuvants derived from ADP-ribosylating bacterial toxins, such as derived from diphtheria toxin (for example, $CRM_{197}$, a non-toxic diphtheria toxin mutant (see, e.g., Bixler et al. (1989) Adv. Exp. Med. Biol. 251:175; and Constantino et al. (1992) Vaccine), pertussis toxin (PT), cholera toxin (CT), the E. coli heat-labile toxins (LT1 and LT2), Pseudomonas endotoxin A, C. botulinum C2 and C3 toxins, as well as toxins from C. perfringens, C spiriforma and C. difficile; saponin adjuvants such as Quil A (U.S. Pat. No. 5,057,540), or particles generated from saponins such as ISCOMs (immunostimulating complexes); cytokines, such as interleukins (e.g., IL-1, IL-2, IL-4; IL-5, IL-6, IL-7, IL-12, etc.), interferons (e.g., gamma interferon), macrophage colony stimulating factor (M-CSF), tumor necrosis factor (TNF), etc; muramyl peptides such as N-acetyl-muramyl-$^L$-threonyl-$^D$-isoglutamine (thr-MDP), N-acetyl-noruramyl-L-alanyl-D-isoglutamine (nor-MDP), N-acetylmuramyl-$^L$-alanyl-$^D$-isoglutaminyl-$^L$-alanine-2-(1'-2'-dipalmitoyl-sn-glycero-3 huydroxyphosphoryloxy)-ethylamine (MTP-PE), etc.; adjuvants derived from the CpG family of molecules, CpG dinucleotides and synthetic oligonucleotides which comprise CpG motifs (see, e.g., Krieg et. al. Nature (1995) 374:546 and Davis et al. J. Immunol. (1998):160:870-876); and synthetic adjuvants such as PCPP (Poly di(carboxylatophenoxy)phosphazene) (Payne et al. Vaccines (1998) 16:92-98). Such adjuvants are commercially available from a number of distributors such as Accurate Chemicals; Ribi Immunechemicals, Hamilton, Mont.; GIBCO; Sigma, St. Louis, Mo.

As explained above, the proteins may be linked to a carrier in order to increase the immunogenicity thereof. Suitable carriers include large, slowly metabolized macromolecules such as proteins, including serum albumins, keyhole limpet hemocyanin, immunoglobulin molecules, thyroglobulin, ovalbumin, and other proteins well known to those skilled in the art; polysaccharides, such as sepharose, agarose, cellulose, cellulose beads and the like; polymeric amino acids such as polyglutamic acid, polylysine, and the like; amino acid copolymers; and inactive virus particles.

The proteins may be used in their native form or their functional group content may be modified by, for example, succinylation of lysine residues or reaction with Cysi-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Other suitable carriers for the proteins of the present invention include VP6 polypeptides of rotaviruses, or functional fragments thereof, as disclosed in U.S. Pat. No. 5,071,651, incorporated herein by reference. Also useful is a fusion product of a viral protein and the subject immunogens made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the proteins of the present invention may be coupled to erythrocytes, preferably the subject's own erythrocytes. Methods of coupling peptides to proteins or cells are known to those of skill in the art.

Furthermore, the proteins may be formulated into vaccine compositions in either neutral or salt forms. Pharmaceutically acceptable salts include the acid addition salts (formed with the free amino groups of the active polypeptides) and which are formed with in-organic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Vaccine formulations will contain a "therapeutically effective amount" of the active ingredient, that is, an amount capable of eliciting an immune response in a subject to which the composition is administered. Such a response will be demonstrated by either a reduction or lack of symptoms normally displayed by an infected host and/or a quicker recovery time.

The exact amount is readily determined by one skilled in the art using standard tests. The protein concentration will typically range from about 1% to about 95% (w/w) of the composition, or even higher or lower if appropriate.

To immunize a subject, the vaccine is generally administered parenterally, usually by intramuscular injection. Other modes of administration, however, such as subcutaneous, intraperitoneal and intravenous injection, are also acceptable. The quantity to be administered depends on the animal to be treated, the capacity of the animal's immune system to synthesize antibodies, and the degree of protection desired. Effective dosages can be readily established by one of ordinary skill in the art through routine trials establishing dose response curves. The subject is immunized by administration of the vaccine in at least one dose, and preferably two doses. Moreover, the animal may be administered as many doses as is required to maintain a state of immunity to infection.

Additional vaccine formulations which are suitable for other modes of administration include suppositories and in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and Hytrel copolymers, swellable polymers such as hydrogels, or resorbable polymers such as collagen and certain polyacids or polyesters such as those used to make resorbable sutures. The proteins can also be delivered using implanted mini-pumps, well known in the art.

The proteins of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel proteins can be constructed as follows. The DNA encoding the particular protein is first inserted into an appropriate vector so that it is adjacent to a vaccinia promoter and flanking vaccinia DNA sequences, such as the sequence encoding thymidine kinase. (TK). This vector is then used to transfect cells which are simultaneously infected With vaccinia Homologous recombination serves to insert the vaccinia promoter plus the gene encoding the instant protein into the viral genome. The resulting TK⁻recombinant can be selected by culturing the cells in the presence of 5-bromodeoxyuridine and picking viral plaques resistant thereto.

An alternative route of administration involves gene therapy or nucleic acid immunization. Thus, nucleotide sequences (and accompanying regulatory elements) encoding the subject proteins can be administered directly to a subject for in vivo translation thereof. Alternatively, gene transfer can be accomplished by transfecting the subject's cells or tissues ex vivo and reintroducing the transformed material into the host. DNA can be directly introduced into the host organism, i.e., by injection (see U.S. Pat. Nos. 5,580, 859 and 5,589,466; International Publication No. WO/90/ 11092; and Wolff et al. (1990) *Science* 247:1465-1468). Liposome-mediated gene transfer can also be accomplished using known methods. See, e.g., U.S. Pat. No. 5,703,055; Hazinski et al. (1991) *Am. J. Respir. Cell Mol. Biol.* 4:206-209; Brigham et al. (1989) *Am. J. Med. Sci.* 298:278-281; Canonico et al. (1991) *Clin. Res.* 39:219A; and Nabel et al. (1990) *Science* 249:1285-1288. Targeting agents, such as antibodies directed against surface antigens expressed on specific cell types, can be covalently conjugated to the liposomal surface so that the nucleic acid can be delivered to specific tissues and cells susceptible to infection.

B.6. Diagnostic Assays

As explained above, the proteins of the present invention may also be used as diagnostics to detect the presence of reactive antibodies of PCVII in a biological sample in order to determine the presence of PCVII infection. For example; the presence of antibodies reactive with the proteins can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound antibody in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a solid phase component (e.g., one or more PCVII proteins) under suitable binding conditions such that the component is sufficiently immobilized to the support. Sometimes, immobilization of the antigen to the support can be enhanced by first coupling the antigen to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigens to the support include polysaccharides, polylactic acids, polyglycolic acids, polymeric amino acids, amino acid copolymers, and the like. Such molecules and methods of coupling these molecules to the antigens, are well known to those of ordinary skill in the art. See, e.g., Brinkley, M. A. *Bioconjugate Chem.* (1992) 3:2-13; Hashida et al., *J. Appl. Biochem.* (1984) 6:56-63; and Anjaneyulu and Staros, *International J. of Peptide and Protein Res.* (1987) 30:117-124.

After reacting the solid support with the solid phase component, any non-immobilized solid-phase components are removed from the support by washing, and the support-bound component is then contacted with a biological sample suspected of containing ligand moieties (e.g., antibodies toward the immobilized antigens) under suitable binding conditions. After washing to remove any non-bound ligand, a secondary binder moiety is added under suitable binding conditions, wherein the secondary binder is capable of associating selectively with the bound ligand. The presence of the secondary binder can then be detected using techniques well known in the art.

More particularly, an ELISA method can be used, wherein the wells of a microtiter plate are coated with a desired protein. A biological sample containing or suspected of containing anti-protein immunoglobulin molecules is then added to the coated wells. After a period of incubation sufficient to allow antibody binding to the immobilized antigen, the plate(s) can be washed to remove unbound moieties and a detectably labeled secondary binding molecule added. The secondary binding molecule is allowed to react with any captured sample antibodies, the plate washed and the presence of the secondary binding molecule detected using methods well known in the art.

Thus, in one particular embodiment, the presence of bound anti-antigen ligands from a biological sample can be readily detected using a secondary binder comprising an antibody directed against the antibody ligands. A number of anti-porcine immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the proteins and antibodies specific for those proteins form complexes under precipitating conditions. In one particular embodiment, proteins can be attached to a solid phase particle (e.g., an agarose bead or the like) using coupling techniques known in the art, such as by direct chemical or indirect coupling. The antigen-coated particle is then contacted under suitable binding conditions with a biological sample suspected of containing antibodies for the proteins. Cross-linking between bound antibodies causes the formation of particle-antigen-antibody complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

In yet a further embodiment, an immunoaffinity matrix can be provided, wherein a polyclonal population of antibodies from a biological sample suspected of containing antibodies to the protein of interest is immobilized to a substrate. In this regard, an initial affinity purification of the sample can be carried out using immobilized antigens. The resultant sample preparation will thus only contain anti-PCVII moieties, avoiding potential nonspecific binding properties in the affinity support. A number of methods of immobilizing immunoglobulins (either intact or in specific fragments) at high yield and good retention of antigen binding activity are known in the art. Not being limited by any particular method, immobilized protein A or protein G can be used to immobilize immunoglobulins.

Accordingly, once the immunoglobulin molecules have been immobilized to provide an immunoaffinity matrix, labeled proteins are contacted with the bound antibodies under suitable binding conditions. After any non-specifically bound antigen has been washed from the immunoaffinity support, the presence of bound antigen can be determined by assaying for label using methods known in the art.

Additionally, antibodies raised to the proteins, rather than the proteins themselves, can be used in the above-described assays in order to detect the presence of antibodies to the proteins in a given sample. These assays are performed essentially as described above and are well known to those of skill in the art.

Furthermore, nucleic acid-based assays may also be conducted. In this regard, using the disclosed PCVII nucleic acid sequences as a basis, oligomers can be prepared which are useful as hybridization probes or PCR primers to detect the presence of the viral genome in, for example, biological samples from subjects suspected of harboring the virus. Oligomers for use in this embodiment of the invention are approximately 8 nucleotides or more in length, preferably at least about 10-12 nucleotides in length, more preferably at least about 15 to 20 nucleotides in length and up to 50 or more nucleotides in length. Preferably, the oligomers derive from regions of the viral genome which lack heterogeneity.

The oligomers are prepared either by excision from the genome, or recombinantly or synthetically. For example, the oligomers can be prepared using routine methods, such automated oligonucleotide synthetic methods.

The oligomers may be used as probes in diagnostic assays. In a representative assay, the biological sample to be analyzed is treated to extract the nucleic acids contained therein. The resulting nucleic acid from the sample may be subjected to gel electrophoresis or other size separation techniques. Alternatively, the nucleic acid sample may be dot-blotted without size separation. The probes are then labeled with a reporter moiety. Suitable labels, and methods for labeling probes, are known in the art and include, for example, radioactive labels incorporated by nick translation or kinasing, biotin, fluorescent probes and chemiluminescent probes. The nucleic acids extracted from the sample are then treated with the labeled probe under hybridization conditions of suitable stringencies.

The probes can be made completely complementary to the targeted PCVII gene sequence. However, when longer probes are used in the diagnostic assays, the amount of complementarity may be less. Generally, conditions of high stringency are used in the assay methods, especially if the probes are, completely or highly complementary. However, lower stringency conditions should be used when targeting regions of heterogeneity. Methods of adjusting stringency are well known in the art. Such adjustments are made during hybridization and the washing procedure and include adjustments to temperature, ionic strength, concentration of formamide and length of time of the reaction. These factors are outlined in e.g., Sambrook et al., supra.

In a more specific embodiment, the above-described method includes the use of PCVII nucleic acid specific probes where two probes (primers) define an internal region of the PCVII genome. In this embodiment, each probe has one strand containing a 3'-end internal to the PCVII nucleic acid internal region. The nucleic acid/probe hybridization complexes are then converted to double-strand probe containing fragments by primer extension reactions. Probe-containing fragments are amplified by successively repeating the steps of (i) denaturing the double-stranded fragments to produce single-stranded fragments, (ii) hybridizing the single strands with the probes to form strand/probe complexes, (iii) generating double-stranded fragments from the strand/probe complexes in the presence of DNA polymerase and all four deoxyribonucleotides, and (iv) repeating steps (i) to (iii) until a desired degree of amplification has been achieved. Amplification products are then identified according to established procedures. The method of the invention may further include a third polynucleotide probe capable of selectively hybridizing to the internal region described above but not to the specific probe/primer sequences used for amplification.

PCR techniques, such as those described above, are well known in the art. See, e.g., *PCR Protocols: A Guide to Methods and Applications* (Academic Press); *PCR A Practical Approach* (IRL press); Saiki et al. (1986) *Nature* 324:163.

Other amplification methods can also be used in the nucleic acid-based assays, such as ligase chain reaction (LCR), PCR, Q-beta replicase, and the like.

Other assays for use herein include the "Bio-Bridge" system which uses terminal deoxynucleotide transferase to add unmodified 3'-poly-dT-tails to a nucleic acid probe (Enzo Biochem. Corp.). The poly dt-tailed probe is hybridized to the target nucleotide sequence, and then to a biotin-modified poly-A. Additionally, EP 124221 describes a DNA hybridization assay wherein the analyte is annealed to a single-stranded DNA probe that is complementary to an enzyme-labelled oligonucleotide, and the resulting tailed duplex is hybridized to an enzyme-labelled oligonucleotide. EP 204510 describes a DNA hybridization assay in which analyte DNA is contacted with a probe that has a tail, such as a poly-dT-tail, an amplifier strand that has a sequence that hybridizes to the tail of the probe, such as a poly-A sequence, and which is capable of binding a plurality of labelled strands. The technique first may involve amplification of the target PCVII sequences in sera to approximately $10^6$ sequences/ml, as described above. The amplified sequence(s) then may be detected using a hybridization assay known in the art.

Furthermore, nucleic acid sequences derived from the PCVII viral genome, may also be used for in situ hybridization assays. Generally, such assays employ formalin-fixed cell culture preparations or tissues, such as lymph node, spleen, tonsil, liver, lung, heart, kidney, pancreas, nasal turbinate, large and small intestine, and the like. See, e.g., Sirinarumitr et al. (1996) *J. Virol. Meth.* 56:149-160, for a description of a suitable in situ hybridization assay.

The above-described assay reagents, including the proteins, antibodies thereto or oligomers, can be provided in kits with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Below are examples of specific embodiments for carrying out the present invention. The examples are offered for illustrative purposes only, and are not intended to limit the scope of the present invention in any way.

C. Experimental

Materials and Methods

Cell Cultures

The Dulac cell line, a PCV-free PK15 derivative, was obtained from Dr. John Ellis (University of Saskatchewan, Saskatoon, Saskatchewan). The Vero cell line was obtained from American Type Culture Collection (ATCC), Manassas, Va. These cells were cultured in media suggested by the ATCC and incubated 37° C. with 5% $C_2$.

Porcine Circoviruses

The classic PCVI was isolated from persistently infected PK15 cells (ATCC CCL33). Isolate PCVII 412 was obtained from lymph nodes of a piglet challenged with the lymph node homogenate from PMWS-affected piglets. This challenged piglet had been diagnosed with PMWS. Isolate PCVII 9741 was isolated from the buffy-coat of peripheral blood from a PMWS-affected piglet of the same herd after the isolation of PCVII 412'. Isolate PCVII B9 was isolated from an affected piglet in a United States swine herd with a PMWS clinical outbreak in the fall of 1997.

Propagation of PCVI

PCVI from persistently infected PK15 cells was grown and purified using a modified method of Tischer et al (1987) *Arch. Virol.* 96:39-57. Briefly, PCV harvested from PK15 cells was used to super-infect a monolayer of PK15 cells at about 1 moi for two hours before the cells were treated with 300 mM D-glucosamine. After washing the cells once, DMEM (Gibco, catalog number 21013) with 5% FBS was added to the cells and the cells were incubated for an additional four days. The infected cells were scraped off and collected after centrifugation at 1500×g for 15 minutes. The cell pellet was then treated with 0.5% of Triton X-114 at 37° C. for 30 minutes. After another low speed centrifugation to remove cellular debris, an equal amount of Freon (Sigma catalog number T-5271) was added to the supernatant and the mixture was homogenized for one minute using a Polytron at maximum speed. The mixture was then centrifuged and the top layer collected and mixed with an equal volume of 0.1 M PBS. The virus pellet was collected after ultra centrifugation into a 20% sucrose cushion at 210,000×g for 30 minutes.

Culture of the Field Isolates (PCVII)

The isolate PCVII 412 was cultured and purified in a similar manner as PCVI, except Dulac cells were used. The isolate PCVII B9 was grown in heterogenic Vero cells transfected with self-ligated fall-length PCR products from the United States PMWS outbreak. Therefore, the possibility of contamination from other pig pathogens was eliminated. The B9-transfected Vero cells were continuously passed and treated with 300 mM D-glucosamine as described above.

Viral DNA Isolation

Viral DNA was extracted from variable sources, including pellets of infected Dulac and Vero cell, peripheral blood buffy-coat cells, tissues from infected animals and serum. The tissue samples were treated with proteinase K and viral DNA was extracted using either phenol/chloroform or Qiagen tissue kit (Qiagen, Santa Clarita, Calif.). DNA from peripheral blood buffy coat cells of heparinized blood and serum was similarly collected using the Qiagen blood kit.

Infection of Piglets

Piglets were derived from specific pathogen-free sows. At one day of age, each piglet received approximately one gram of lymph nodes collected from PMWS-affected piglets. The tissue homogenate was distributed equally between the oral and intraperitoneal routes. Ten piglets were used in each of the experimental groups and observed daily for 7 weeks. Two groups were challenged and 2 were uninfected controls. Two groups, one challenged and one control, were also treated with cyclosporin A (2 mg/kg) at Day 0 and Day 14. The piglets were fed canned milk (Carnation) and water (50:50) until they self-weaned to high nutrient density commercially prepared feed.

PCR, Cloning and Sequencing of the Field PCV Isolates

A two-step approach was used for the initial cloning of isolate PCVII 412 viral genomic DNA. A primer that hybridized to the conserved loop stem sequences, Loops (Table 1), was designed to perform a single-primed PCR taking advantage of the complementary sequences and the circular nature of PCV genomic DNA. The PCR reaction for the single-primed PCR was a two-stage process. The first stage consisted of 5 cycles of denaturing at 94° C. for 1 minute, annealing at 37° C. for 30 seconds and extension at 72° C. for 2 minutes. The second stage consisted of 25 cycles of a similar program except the annealing temperature was increased to 52° C. The PCR products were cloned into a TA cloning vector (Invitrogen, Carlsbad, Calif.). Both strands of three different clones were sequenced to ensure sequence fidelity. Based on the sequences obtained, primer 1000-and R1F were designed in the noncoding region of the viral DNA sequences and used to clone the full-length viral genome. The sequences of all the primers used in this study are shown in Table 1. The sequences of the loop region were then obtained from the full-length clone. Sequences of isolate PCVII 9741 and PCVII B9 were obtained from purified PCR products. Automated DNA sequencing performed by Plant Biotechnology Institute of NRC, Canada was used with several internal primers. The sequences of isolates PCVII 412 (AF085695), PCVII 9741 (AF086835) and PCVII B9 (AF086834) have been deposited with the National Center for Biotechnology Information (NCBI).

TABLE 1

Sequences of Primers Used in the Studies

| Primer Name | Primer Sequence | SEQ ID NO: |
|---|---|---|
| Loop− | ACTACAGCAGCGCACTTC | 13 |
| 1000− | AAAAAGACTCAGTAATTTATTTCATATGG | 14 |
| R1F | ATCACTTCGTAATGGTTTTTATT | 15 |
| 1710+ | TGCGGTAACGCCTCCTTG | 16 |
| 850− | CTACAGCTGGGACAGCAGTTG | 17 |
| 1100+ | CATACATGGTTACACGGATATTG | 18 |
| 1570− | CCGCACCTTCGGATATACTG | 19 |
| 1230− | TCCCGTTACTTCACACCCAA | 22 |
| 400+ | CCTGTCTACTGCTGTGAGTA | 23 |

Sequence Analyses

The sequences of other circoviruses were obtained from NCBI. Various public domains were used for the sequence analysis, such as Biology workbench, Blast search, DNA/protein analysis tools, etc. The sequence alignments were generated using Clustal W program and phylogenetic trees were created by PAUP 3.1 program (David L. Swofford, Laboratory of Molecular Systematics, MRC534, MRC at Smithsonian Institution, Washington, D.C.).

Multiplex PCR

Two sets of primers were designed to identify the PCV group-specific sequences and strain-specific sequences. The primer pair 1710+/850− is PCV-group specific and 1100+/1570− is the novel PCV strain-specific pair, which differentiates the novel PCV from the one derived from PK15 cells. The two sets of primers have similar annealing temperatures for the PCR reaction and were used together at 0.5 µM concentration in a standard hot start PCR reaction. Either Ampli Taq Gold (Perkin Elmer) or Plentinum Taq (Gibco) was used.

Antiserum

The standard Berlin rabbit anti-PCVI antibody was kindly provided by Dr. Tischer (Koch Institute, Berlin, FRG). Rabbit-anti-PCVII 412 pooled serum was obtained from two rabbits injected with purified isolate PCVII 412 at 50 µg/dose in an oil-in-water emulsion. The injection was repeated 3 times at 21-day intervals. Pig anti-PMWS serum was collected from convalescent pigs from PMWS affected herds.

ELISA

Purified PCV was diluted in sodium carbonate buffer (0.05 M) pH 9.6 to a concentration of 0.5 µg per 100 µL and used to coat Immulon II plates (Dynatech Laboratories, Inc.). The plates were washed six times with TTBS (20 mM Tris-HCl, 500 mM NaCl, 0.05% of Tween 20, pH 7.5) before serially diluted primary rabbit or pig antibody was added. After six washes with TTBS, alkaline phosphatase-conjugated secondary antibodies (1/5000 dilution), either anti-rabbit or anti-pig (Kirkegaard & Perry), were added. Plates were developed with 100 µL/well of p-Nitrophenyl Phosphate (PNPP, 3 g/L) in 1 M diethanolamine, 0.5 $MgCl_2$, pH 9.8 and the plates were read on an ELISA reader (BioRad) at 405/490 nm.

FACS Analysis of lymphocyte surface markers

Blood samples were collected from PMWS affected piglets in the field and negative control. The RBC was lysed and WBC was stained with anti-pig CD3, CD4 and CD8 monoclonal antibodies, and followed by fluorescence labeled anti-mouse secondary antibody. The specifically labeled cells were fixed with 2% formaldehyde and 5000 cells were counted using FACS system (Becton Dickinson).

The present invention will now be more fully described with reference to the following non-limiting Examples.

EXAMPLES

Example 1

PMWS Reproduction

PMWS has not been reproduced under controlled conditions, nor have etiology studies been performed. In order to determine the causative agent of this disease, a number of tissues were collected from PMWS-affected pigs, as described above in Materials and Methods, and studied. Lymph nodes displayed the most apparent gross lesions, histopathological changes and circovirus infection was confirmed by immunostaining. Accordingly, the lymph nodes were used in the challenge experiments described above.

The challenge experiments, conducted as described in Materials and Methods were successful in producing PMWS in pigs. In particular, some piglets died of the infection and asymptomatically infected piglets developed PMWS-like microscopic lesions by the end of the trial.

In another challenge experiment, the starting material used was lung tissue of pig with chronic wasting and lymph node enlargement. These clinical signs are characteristic of PMWS. The tissue was combined with sterile 0.1 M phosphate-buffered saline (PBS) and homogenized by passage through a polytron mixer. The crude tissue homogenate was used to challenge pigs. In particular, a total of 40 piglets (approximately 1 day of age) were randomly (balanced by litter of birth, gender and body weight) assigned to "tissue challenge," "tissue challenge with Cyclosporin-A," "control," or "Cyclosporin-A" treatment groups. The cyclosporin treatment had no clinical or hematological effect on the treated pigs except that cyclosporin was detected in the blood of those pigs three hours after the drug was administered. Hence, groups were collapsed across cyclosporin treatment for analysis.

In general, postmortem signs of PMWS disease in the challenged pigs included enlarged lymph nodes and incomplete collapse of lung tissue. Postmortem signs of PMWS disease were detected in significantly (p<0.01; two-tailed Fishers exact-test) more pigs in the group treated with tissue extract (7 pigs out of 9) than in the group treated with placebo (2 pigs out of 18). The average daily gain in the group treated by injection of tissue extract (212 g/d) was not substantially different from the group given the placebo (202 g/d).

Blood samples were obtained throughout the experiment and tissue samples were taken postmortem. The samples were tested for PCVII viral DNA by PCR, using PCR primers 1230– and 400+ (Table 1) which resulted in an 830 base pair product. Four of the pigs given the lung tissue extract had positive blood samples; whereas none of the pigs given placebo had PCVII DNA detected in their blood. PCVII was detected in one or more tissues from 7 of the 8 surviving pigs in the "virus challenge" treatment group whereas all tissues from pigs in the control group were negative for PCVII. Contingency table analysis showed a significant difference (p<0.001; two-tailed Fishers exact-test).

In another challenge experiment, lung tissue of pig with chronic wasting and lymph node enlargement was collected and tissue debris removed by centrifugation (8000 rpm for 30 minutes). The supernatant was applied to a cesium chloride step-gradient and centrifuged at 100,00×g. Bands appeared between 41% $CsCl_2$ (1.28 gm/ml) and 63% (1.40 gm/ml). These bands were applied to a 30% $CsCl_2$ "foot" and centrifuged for 2 hours at 100,000×g. The pellet was resuspended in 15 mL of sterile 0.1 M PBS.

A total of 20 weaned piglets (approximately three weeks of age) were randomly (balanced by litter of birth, gender and body weight) assigned to "control" or "virus challenge" treatment groups. Pigs were weaned on Day 0 at approximately three weeks of age. In general, clinical signs of PMWS disease included enlarged lymph nodes and wasting or poor growth. Enlarged lymph nodes were detected in significantly (p<0.02; two-tailed Fisher exact-test) more pigs in the group treated with virus (7 pigs) than in the group treated with placebo (1 pig). The average daily gain in the group treated by virus injection (580 gm/d) tended to be less than the group given the placebo (616 gm/d), but the difference was not significant (p=0.17; two-tailed paired t-Test). There was no difference between groups in the relative mass of internal organs (liver, lung, heart, spleen, kidneys).

Blood samples that were obtained throughout the experiment and tissue samples that were taken postmortem were tested for PCVII viral DNA using the PCR techniques described above.

All blood samples including those taken just prior to euthanasia were negative for PCVII. PCVII was detected in one or more tissues for 8 of the 10 pigs in the "virus challenge" treatment group whereas all tested tissues from pigs in the control group were negative for PCVII. Contingency table analysis showed that this was a significant difference (p<0.001; two-tailed Fishers exact-test).

In conclusion, these experiments confirm that injection of weaned piglets with tissue extracts and gradient-purified viral material containing PCVII results in infection of multiple tissues. The infection persists for a duration of at least eight weeks.

Example 2

Isolation and Propagation of PCVII

To determine the presence of an infectious causative agent(s) for PMWS, various tissues from pig #412, an experimentally challenged piglet sacrificed 21 days post-infection, were used for viral isolation. After continued passage of lymph node samples from pig #412 in Dulac cells, virus accumulation or adaptation was observed. A unique pattern of cytopathic effect initially developed, followed by increasing virus titer, as determined by ELISA using the standard Berlin anti-PCV antibody, as described above.

The existence of circovirus in Dulac cells infected with isolate PCVII 412 was then detected by electron microscopic examination. After six passages, viral structure proteins could be detected consistently, using a western blot assay.

Example 3

Specific Anti-PCVII Antibodies in Asymptomatically Infected and Convalescent Piglets in PMWS-Affected Herds Because it appeared that porcine circoviruses possessed some heterogeneity, ELISAs were performed using sera of piglets, collected from a herd with a PMWS outbreak, against the PCV and isolate PCVII 412 virus. Most of the asymptomatically PCVII-infected and convalescent piglets developed specific antibodies against FCVII, not PCVI.

Example 4

Isolation, Cloning and Sequencing of PCVII Virus and Viral Genomic DNA

In order to explore genetic differences between the two strains of porcine circoviruses, viral DNA was extracted from infected Dulac cells. Considering the possible genetic, unrelatedness between PCVI and PCVII, the approach was to design primer(s) from the most conserved region. Previous analysis of the PK15 PCV DNA sequences (Mankertz et al. (1997) J. Gen. Virol. 71:2562-2566; Meehan et al. (1997) J. Gen. Virol. 78:221-227) revealed a stem loop structure in the origin of replication. A single primer, targeting the inverted repeat sequence of the stem loop region, Loop⁻, was designed because of the highly conserved nature of this important domain. The amplification of the PCVII 412 viral DNA by single primer PCR was successful. After cloning into a TA cloning vector, the viral genomic sequence was obtained by automated sequencing from several clones and both senses to ensure fidelity. The actual sequence of the stem loop or primer region was then obtained from a second fill-length clone generated by primers of 1000– and R1F from the only non-coding region of the virus. The nucleotide sequence for PMWS 412 is shown in the top line of FIGS. 2A-2C.

Using similar primers, other PCVII isolates, including PCVII-9741 from the same herd as PCVII 412, and PCVII B9 from a PMWS outbreak in the United States, were obtained. These strains were sequenced and compared to PCVII 412 and PCVI. See FIGS. 2A-2C for a comparison of PCVII 412 with PCVI and FIGS. 4A-4B for comparisons of the PCVII 412 sequence with the various PCV isolates.

The results of a phylogenetic analysis using the PAUP 3.1 program suggested that the new PMWS isolates were closely related and in a different cluster with PCVI. These isolates were therefore termed "PCVII" isolates. The percent nucleotide sequence homologies among isolates of the novel porcine circovirus were more than 99% identical. In contrast, comparison of these nucleotide sequences with the PK15 PCVI showed only 75.8% overall nucleotide sequence homology. Comparative analysis of nucleotide sequences in different regions further revealed that the putative replication-associated protein gene of these two viruses share 81.4% homology, while the nucleotide sequences of the other large ORF was only 67.6% homologous.

Furthermore, nucleotide insertions and deletions (indels) were found in three regions. There are 13 base insertions in the new isolates between PCVI sequence 38-61 that flank the start codon for the putative 35.8 kd protein encoded by ORF 1. The area of PCVI 915-1033, containing 15 base indels, was at the ends and the joint region of the two largest ORFs (the other ORF was antisense) of the porcine circoviruses. The third region, covering PCVI sequence from 1529-1735 with 15 base indels, locates at the amino end of a putative 27.8 kd protein encoded by ORF 6. PCVI sequences were also compared with the available sequences of the rest of the members of Circoviridae. PCVI is more closely related to banana bunch top virus (BBTV), a plant virus, than to chicken anemia virus (CAV) and beak and feather disease virus (BFDV) (both of which are avian circoviruses).

The gene map of isolate PCVII 412 is shown in FIG. 1. There are a total of six potential ORFs encoding proteins larger than 50 amino acid residues. A comparison between PCVII 412 and PK15 PCVI revealed homologies in four of the ORFs (Table 2). The function of the 35.8 kd, namely the putative DNA replicase protein, has been previously predicted (Meehan et al. (1997) J. Gen. Virol. 78:221-227). Analysis of these proteins predicted that both of the 35.8 kd and the antisense 27.8 kd proteins are nuclear proteins. Nucleotide sequence analysis also indicated that the start codons for the two proteins are within 33 bases of the origin of replication, which could also be the promoter. In addition, both ORFs ended with legitimate stop codons and poly A tail signals. Since some of the predicted proteins (based on size) could be found in western blots, these findings suggest that porcine circoviral mRNA can be transcribed from both senses of the replicated forms. However, there is no coding sequence long enough to code for the common 31 kd protein and the additional 20 kd protein for the PCVII 412 isolate detected by western blot analysis. This suggests that post-translational cleavage and/or RNA splicing may be involved in the expression of some of the porcine circovirus proteins.

TABLE 2

Putative Amino Acid Sequence Comparison Between PK15 PCVI and PCVII 412

| Open reading frames | | Sequence Homology | Predicted |
|---|---|---|---|
| PCVI | 412 | % PCVI/412 | Localization and Function |
| 47-983 (ORF 1) | 51-992 (ORF 1) | 83.5 | Nucleus, putative Rep protein |
| 1723-1024 (ORF 6) | 1735-1037 (ORF 6) | 66.4 | Nucleus |
| 552-207 (ORF 4) | 565-389 (ORF 3) | 40.9 | Endoplasmic Reticulum |

TABLE 2-continued

Putative Amino Acid Sequence Comparison Between PK15 PCVI and PCVII 412

| Open reading frames | | Sequence Homology | Predicted |
|---|---|---|---|
| PCVI | 412 | % PCVI/412 | Localization and Function |
| 658-40 (ORF 3) | 671-359 (ORF 2) | 29.1 | Microbody |

Example 5

Purification of PCVII Using Molecular Cloning Method

Dulac cells were found to be infected with porcine retrovirus which is also found in many pig origin cell lines. In addition, other porcine pathogens were also found inconsistently associated with PCVII in PMWS-affected piglets. Thus, to obtain pure PCVII cultures, genetically cloned PCVII DNA was transferred to the susceptible non-porcine origin Vero cells using liposomes. After two passages, amplified PCV antigens were detected in the cells. The PCVII was seen to replicate and accumulate in the nuclei and was released into cytoplasm and other cells during cell mitosis.

Example 6

Multiplex PCR in PCVI Identification and PMWS Diagnosis

In order to differentiate the two strains of porcine circoviruses, PCVI and PCVII, two sets of primers were designed based upon the comparative analysis of the viral DNA sequences. The PCV group-specific pair of 1710+/850, and isolate PCVII 412 strain-specific 1100+/1570−, were used in multiplex PCR for testing field samples. These primer sets were used with frozen tissues and buffy coat cells of peripheral blood. As judged by the multiplex PCR, using those primer sets, not only was PCVII infection identified in these samples but the genetic relatedness of the field samples was also determined. The presence of circovirus was later confirmed by electron microscopy.

The potency of this diagnostic method was further tested with another group of samples collected from a PMWS-affected herd (see FIG. 5). The PCVII DNA sequences could also be identified in almost all the tissues in PMWS-affected piglets. (FIG. 6).

Example 7

PCVII Viremia Prior to and During PMWS Outbreak

The development of PCR using serum enabled us to test the PCVII viremia in a swineherd showing specific anti-PCVII antibody. A group of 23 piglets was monitored from the age of one day until seven weeks and samples were collected at approximately two week intervals. A full-course of PCVII viremia and PMWS outbreak were observed, as indicated by the appearance to disappearance of the PCVII viremia which was detected in 9 of the 23 piglets. Most of piglets which showed PCVII viremia developed PMWS with some exhibiting severe PMWS. Table 3 shows the manifestation of PMWS in a typical pig. Gross lesions were found in most organs and tissues (Table 3).

TABLE 3

Clinical, Histological, VIrological and Immunological Report of a Typical PMWS Affected Piglet

| PMWS Pig | Gross appearance | Histopath | PCR |
| --- | --- | --- | --- |
| H254 | Spine, hairy, disinterested and wobbled | | |
| Saliva | ND | ND | ND |
| Urine | Pale/clear | ND | + |
| Bile | Thin, not viscid | ND | + |
| Feces | Scant but normal | ND | + |
| Serum | Normal | ND | + |
| Plasma | Yellow | ND | + |
| Skin | Hint of yellow | | + |
| Fat | Little/no fat | | + |
| Muscle | Normal | | + |
| Tongue | Normal | Glossitis | + |
| Tonsil | Small crypts | Lymphocyte depletion | + |
| Cerv. LN | Enlarged | Lymphocyte depletion | + |
| Med. LN | Very large, dark surface, yellow center | Lymphocyte depletion | + |
| Mesenteric LN | Very enlarged, dark and wet | Lymphocyte depletion | + |
| Inguinal LN | Large, dark and wet | Lymphocyte depletion | + |
| Spleen | Small and thin | Lymphocyte depletion | + |
| Thymus | Small and difficult to find | ND | + |
| Treachea | Normal | Metaplasia adenitis | + |
| Lung | A, M lobes 80% atelectasis; firm texture mottles and spots thoughout all lobes | Interstitial Pneumonia | + |
| Heart | Thin and flabby | | + |
| Liver | "Camouflage" pattern mottling | | + |
| Gall Bladder | Normal, moderately full | | + |
| Pancreas | Normal | | + |
| Adrenal | Normal | Focal adrenalitis | + |
| Brain | Normal | Meningitis | + |
| Eye | Normal, white sclera | | + |
| Stomach | Normal, full of feed | | + |
| Small intestine | Normal | Peyers Patch | + |
| Large intestine | Normal, sandy/gritty contents | Submucosal inflam | + |
| Kidney | Enlarged, dark and no pus | Interstitial nephritis | + |
| Urinary bladder | Normal | | + |
| | | Ref mg × 10$^9$/L | |
| CBC | WBC: 20.1 | 11.0-22.0 | |
| | Segs: 62% or 12.462 | 3.08-10.4 | |
| | Lymphs: 29.0% or 5.829 | 4.29-43.6 | |
| FACS | CD3: 52.1% | 55% | |
| | CD4: 9.0% | 30% | |
| | CD8: 66.5% | 15% | |

Example 8

Host Immune System Dysfunction in PMWS Affected Piglets

It is interesting that while lymphocyte infiltration was discovered in most of the tissues, lymphocyte depletion was consistently found in all the lymphoid tissues (Table 3). Decreased CD4 cell, and increased CD8 cells were also seen, while CD3 cells remained relatively stable (Table 4, mean numbers are from two PMWS affected and 40 negative control piglets). These changes resulted in CD4/CD8 ratio which drastically dropped from 1.58 to 0.13. These finding suggested that PCVII could induce host immune system malfunction and therefore suppress the host immune responses to PCVII and possibly other pathogens. Thus, PMWS appears to be a disease of immunodeficiency in piglets.

TABLE 4

Lymphocyte Surface Markers of PMWS Affected and Control 6-week-old Piglets

| | CD3 | CD4 | CD8 | CD4/CD8 Ratio |
| --- | --- | --- | --- | --- |
| PMWS | 59.88 | 8.85 | 67.6 | 0.13 |
| Control | 53.46 | 24.02 | 15.18 | 1.58 |

Deposits of Strains Useful in Practicing the Invention

A deposit of biologically pure cultures of clone B9WTA, a clone including the full-length nucleic acid sequence of PCVII B9 as depicted in FIGS. 4A-4B, was made with the American Type Culture Collection, 10801 University Boulevard, Manassas, Va. on May 5, 1999 and assigned Accession No. PTA-24. The accession number indicated was assigned after successful viability testing, and the requisite fees were paid. The deposits were made under the provisions of the Budapest Treaty on the International Recognition of the Deposit of Microorganisms for the Purpose of Patent Procedure and the Regulations thereunder (Budapest Treaty). This assures maintenance of viable cultures for a period of thirty (30) years from the date of deposit. The organisms will be made available by the ATCC under the terms of the Budapest Treaty, which assures permanent and unrestricted availability of the progeny to one determined by the U.S. Commissioner of Patents and Trademarks to be entitled thereto according to 35 U.S.C.§122 and the Commissioner's rules pursuant thereto (including 37 C.F.R. §1.12 with particular reference to 8860G 638). Upon the granting of a patent, all restrictions on the availability to the public of the deposited cultures will be irrevocably removed.

These deposits, are provided merely as convenience to those of skill in the art, and are not an admission that a deposit is required under 35 U.S.C. §112. The nucleic acid sequences of these genes, as well as the amino acid sequences of the molecules encoded thereby, are incorporated herein by reference and are controlling in the event of any conflict with the description herein.

\*\*\*

Having thus described in detail preferred embodiments of the present invention, it is to be understood that the invention defined by the appended claims is not to be limited to particular details set forth in the above description, as many apparent variations thereof are possible without departing from the spirit or scope of the present invention. Modifications and variations of the method and apparatuses described herein will be obvious to those skilled in the art, and are intended to be encompassed by the following claims.

We claim:

1. A baculovirus containing and expressing an exogenous nucleotide sequence, wherein the nucleotide sequence encodes an immunogenic polypeptide having at least 85% identity to the polypeptide encoded by ORF 6 (SEQ ID NO:5).

2. The baculovirus of claim 1, wherein the immunogenic polypeptide has at least 90% identity to the polypeptide encoded by ORF 6 (SEQ ID NO:5).

3. The baculovirus of claim 1, wherein the immunogenic polypeptide has at least 95% identity to the polypeptide encoded by ORF 6 (SEQ ID NO:5).

4. The baculovirus of claim 1, wherein the immunogenic polypeptide has at least 98% identity to the polypeptide encoded by ORF 6 (SEQ ID NO:5).

5. An isolated host cell transformed with the baculovirus of claim 1.

6. A method for producing an immunogenic polypeptide having at least 85% identity to the polypeptide encoded by ORF 6 (SEQ ID NO:5) comprising transforming a host cell with the baculovirus of claim 1 and culturing the transformed host cell under conditions whereby the immunogenic polypeptide is expressed.

7. The method of claim 6, wherein the immunogenic polypeptide has at least 90% identity to the polypeptide encoded by ORF 6 (SEQ ID NO:5).

8. The method of claim 6, wherein the immunogenic polypeptide has at least 95% identity to the polypeptide encoded by ORF 6 (SEQ ID NO:5).

9. The method of claim 6, wherein the immunogenic polypeptide has at least 98% identity to the polypeptide encoded by ORF 6 (SEQ ID NO:5).

10. The method of claim 6, further comprising isolating the immunogenic polypeptide from a cell lysate of the transformed host cell.

11. The method of claim 10, further comprising purifying the immunogenic polypeptide.

12. The method of claim 6, further comprising purifying the immunogenic polypeptide from media in which the transformed host cell was cultured.

13. A baculovirus containing and expressing an exogenous nucleotide sequence, wherein the nucleotide sequence encodes an immunogenic polypeptide comprising at least 25 contiguous amino acids of the polypeptide encoded by ORF 6 (SEQ ID NO:5).

14. An isolated host cell transformed with the baculovirus of claim 13.

15. A method for producing an immunogenic polypeptide comprising at least 25 contiguous amino acids of the polypeptide encoded by ORF 6 (SEQ ID NO:5) comprising transforming a host cell with the baculovirus of claim 13 and culturing the transformed host cell under conditions whereby the immunogenic polypeptide is expressed.

16. The method of claim 15, further comprising isolating the immunogenic polypeptide from a cell lysate of the transformed host cell.

17. The method of claim 16, further comprising purifying the immunogenic polypeptide.

18. The method of claim 15, further comprising purifying the immunogenic polypeptide from media in which the transformed host cell was cultured.

* * * * *

SEQUENCE LISTING

<160> NUMBER OF SEQ ID NOS: 24

<210> SEQ ID NO 1
<211> LENGTH: 1768
<212> TYPE: DNA
<213> ORGANISM: Porcine Circovirus Type II

<400> SEQUENCE: 1

```
accagcgcac ttcggcagcg gcagcacctc ggcagcacct cagcagcaac atgcccagca      60
agaagaatgg aagaagcgga ccccaaccac ataaaaggtg ggtgttcacg ctgaataatc     120
cttccgaaga cgagcgcaag aaaatacggg agctcccaat ctccctattt gattatttta    180
ttgttggcga ggagggtaat gaggaaggac gaacacctca cctccagggg ttcgctaatt    240
ttgtgaagaa gcaaactttt aataaagtga agtggtattt gggtgcccgc tgccacatcg    300
agaaagccaa aggaactgat cagcagaata agaatattg cagtaaagaa ggcaacttac    360
ttattgaatg tggagctcct cgatctcaag gacaacggag tgacctgtct actgctgtga    420
gtaccttgtt ggagagcggg attctggtga ccgttgcaaa gcagcaccct gtaacgtttg    480
tcaaaaattt ccgcgggctg gctgaacttt tgaaagtgag cgggaaaatg caaaagcgtg    540
attggaaaac caatgtacac ttcattgtgg ggccacctgg gtgtggtaaa agcaaatggg    600
ctgctaattt tgcaaacccg gaaaccacat actggaaacc acctaaaaac aagtggtggg    660
atggttacca tggtgaaaaa gtggttgtta ttgatgactt ttatggctgg ctgccgtggg    720
atgatctact gagactgtgt gatcgatatc cattgactgt aaaaactaaa ggtggaactg    780
tacctttttt ggcccgcagt attctgatta ccagcaatca gaccccgttg gaatggtact    840
cctcaactgc tgtcccagct gtagaagctc tctatcggag gattacttcc ttggtatttt    900
ggaagaatgc tacaaaacaa tccacggagg aagggggcca gttcgtcacc ctttcccccc    960
catgccctga atttccatat gaaataaatt actgagtctt ttttatcact tcgtaatggt   1020
ttttattatt catttagggt tcaagtgggg ggtctttaag attaaattct ctgaattgta   1080
catacatggt tacacggata ttgtagtcct ggtcgtattt actgttttcg aacgcagtgc   1140
cgaggcctac gtggtccaca tttccagagg tttgtagcct cagccaaagc tgattccttt   1200
tgttatttgg ttggaagtaa tcaatagtgg agtcaagaac aggtttgggt gtgaagtaac   1260
gggagtggta ggagaagggt tgggggattg tatggcggga ggagtagttt acatatgggt   1320
cataggttag ggctgtggcc tttgttacaa agttatcatc taaaataaca gcagtggagc   1380
ccactcccct atcaccctgg gtgatggggg agcaaggcca gaattcaacc ttaacctttc   1440
ttattctgta gtattcaaag ggtatagaga tttttgttggt ccccctccc ggggaacaa    1500
agtcgtcaat tttaaatctc atcatgtcca ccgcccagga gggcgttgtg actgtggtac   1560
gcttgacagt atatccgaag gtgcgggaga ggcgggtgtt gaagatgcca tttttccttc   1620
tccaacggta gcggtggcgg gggtggacga gccaggggcg gcggcggagg atctggccaa   1680
```

| | | | | |
|---|---|---|---|---|
| gatggctgcg | ggggcggtgt | cttcttctgc | ggtaacgcct | ccttggatac gtcatagctg 1740 |
| aaaacgaaag | aagtgcgctg | taagtatt | | 1768 |

```
<210> SEQ ID NO 2
<211> LENGTH: 1759
<212> TYPE: DNA
<213> ORGANISM: Porcine Circovirus Type I

<400> SEQUENCE: 2
```

| | | | | |
|---|---|---|---|---|
| accagcgcac | ttcggcagcg | gcagcacctc | ggcagcgtca | gtgaaaatgc caagcaagaa 60 |
| aagcggcccg | caaccccata | agaggtgggt | gttcacccett | aataatcctt ccgaggagga 120 |
| gaaaaacaaa | atacgggagc | ttccaatctc | cctttttgat | tattttgttt gcggagagga 180 |
| aggtttggaa | gagggtagaa | ctcctcacct | ccagggggttt | gcgaattttg ctaagaagca 240 |
| gacttttaac | aaggtgaagt | ggtatttttgg | tgcccgctgc | cacatcgaga aagcgaaagg 300 |
| aaccgaccag | cagaataaag | aatactgcag | taaagaaggc | cacatactta tcgagtgtgg 360 |
| agctccgcgg | aaccagggga | agcgcagcga | cctgtctact | gctgtgagta ccctttttgga 420 |
| gacggggtct | ttggtgactg | tagccgagca | gttccctgta | acgtatgtga aaatttccg 480 |
| cgggctggct | gaacttttga | aagtgagcgg | aaagatgcag | cagcgtgatt ggaagacagc 540 |
| tgtacacgtc | atagtgggcc | cgcccggttg | tgggaagagc | cagtgggccc gtaattttgc 600 |
| tgagcctagg | gacacctact | ggaagcctag | tagaaataag | tggtgggatg gatatcatgg 660 |
| agaagaagtt | gttgttttgg | atgattttta | tggctggtta | ccttgggatg atctactgag 720 |
| actgtgtgac | cggtatccat | tgactgtaga | gactaaaggg | ggtactgttc cttttttggc 780 |
| ccgcagtatt | ttgattacca | gcaatcaggc | cccccaggaa | tggtactcct caactgctgt 840 |
| cccagctgta | gaagctctct | atcggaggat | tactactttg | caattttgga agactgctgg 900 |
| agaacaatcc | acgaggtac | ccgaaggccg | atttgaagca | gtggaccac cctgtgccct 960 |
| tttcccatat | aaaataaatt | actgagtctt | ttttgttatc | acatcgtaat ggttttatt 1020 |
| tttatttatt | tagagggtct | tttaggataa | attctctgaa | ttgtacataa atagtcagcc 1080 |
| ttaccacata | attttgggct | gtggctgcat | tttggagcgc | atagccgagg cctgtgtgct 1140 |
| cgacattggt | gtgggtattt | aaatggagcc | acagctggtt | tcttttatta tttgggtgga 1200 |
| accaatcaat | tgtttggtcc | agctcaggtt | tggggggtgaa | gtacctggag tggtaggtaa 1260 |
| agggctgcct | tatggtgtgg | cgggaggagt | agttaatata | ggggtcatag gccaagttgg 1320 |
| tggaggggggt | tacaaagttg | gcatccaaga | taacaacagt | ggacccaaca cctctttgat 1380 |
| tagaggtgat | ggggtctctg | gggtaaaatt | catatttagc | cttttctaata cggtagtatt 1440 |
| ggaaaggtag | gggtaggggg | ttggtgccgc | ctgaggggggg | gaggaactgg ccgatgttga 1500 |
| atttgaggta | gttaacattc | caagatggct | gcgagtatcc | tcctttatg gtgagtacaa 1560 |
| attctgtaga | aaggcgggaa | ttgaagatac | ccgtcttttcg | cgccatctg taacggtttc 1620 |
| tgaaggcggg | gtgtgccaaa | tatggtcttc | tccggaggat | gtttccaaga tggctgcggg 1680 |
| ggcgggtcct | tcttctgcgg | taacgcctcc | ttggccacgt | catcctataa aagtgaaaga 1740 |
| agtgcgctgc | tgtagtatt | | | 1759 |

```
<210> SEQ ID NO 3
<211> LENGTH: 314
<212> TYPE: PRT
<213> ORGANISM: Porcine Circovirus Type II

<400> SEQUENCE: 3
```

Met Pro Ser Lys Lys Asn Gly Arg Ser Gly Pro Gln Pro His Lys Arg
1               5                   10                  15

Trp Val Phe Thr Leu Asn Asn Pro Ser Glu Asp Glu Arg Lys Lys Ile
                20                  25                  30

Arg Glu Leu Pro Ile Ser Leu Phe Asp Tyr Phe Ile Val Gly Glu Glu
            35                  40                  45

Gly Asn Glu Glu Gly Arg Thr Pro His Leu Gln Gly Phe Ala Asn Phe
    50                  55                  60

Val Lys Lys Gln Thr Phe Asn Lys Val Lys Trp Tyr Leu Gly Ala Arg
65              70                  75                  80

Cys His Ile Glu Lys Ala Lys Gly Thr Asp Gln Gln Asn Lys Glu Tyr
                85                  90                  95

Cys Ser Lys Glu Gly Asn Leu Leu Ile Glu Cys Gly Ala Pro Arg Ser
                100                 105                 110

Gln Gly Gln Arg Ser Asp Leu Ser Thr Ala Val Ser Thr Leu Leu Glu
            115                 120                 125

Ser Gly Ile Leu Val Thr Val Ala Glu Gln His Pro Val Thr Phe Val
    130                 135                 140

Lys Asn Phe Arg Gly Leu Ala Glu Leu Leu Lys Val Ser Gly Lys Met
145                 150                 155                 160

Gln Lys Arg Asp Trp Lys Thr Asn Val His Phe Ile Val Gly Pro Pro
                165                 170                 175

Gly Cys Gly Lys Ser Lys Trp Ala Ala Asn Phe Ala Asn Pro Glu Thr
                180                 185                 190

Thr Tyr Trp Lys Pro Pro Lys Asn Lys Trp Trp Asp Gly Tyr His Gly
            195                 200                 205

Glu Lys Val Val Val Ile Asp Asp Phe Tyr Gly Trp Leu Pro Trp Asp
    210                 215                 220

Asp Leu Leu Arg Leu Cys Asp Arg Tyr Pro Leu Thr Val Lys Thr Lys
225                 230                 235                 240

Gly Gly Thr Val Pro Phe Leu Ala Arg Ser Ile Leu Ile Thr Ser Asn
                245                 250                 255

Gln Thr Pro Leu Glu Trp Tyr Ser Ser Thr Ala Val Pro Ala Val Glu
            260                 265                 270

Ala Leu Tyr Arg Arg Ile Thr Ser Leu Val Phe Trp Lys Asn Ala Thr
    275                 280                 285

Lys Gln Ser Thr Glu Glu Gly Gly Gln Phe Val Thr Leu Ser Pro Pro
290                 295                 300

Cys Pro Glu Phe Pro Tyr Glu Ile Asn Tyr
305                 310

<210> SEQ ID NO 4
<211> LENGTH: 312
<212> TYPE: PRT
<213> ORGANISM: Porcine Circovirus Type I

<400> SEQUENCE: 4

Met Pro Ser Lys Lys Ser Gly Pro Gln Pro His Lys Arg Trp Val Phe
1               5                   10                  15

Thr Leu Asn Asn Pro Ser Glu Glu Glu Lys Asn Lys Ile Arg Glu Leu
                20                  25                  30

Pro Ile Ser Leu Phe Asp Tyr Phe Val Cys Gly Glu Glu Gly Leu Glu
            35                  40                  45

Glu Gly Arg Thr Pro His Leu Gln Gly Phe Ala Asn Phe Ala Lys Lys

```
                50                  55                  60
Gln Thr Phe Asn Lys Val Lys Trp Tyr Phe Gly Ala Arg Cys His Ile
 65                  70                  75                  80

Glu Lys Ala Lys Gly Thr Asp Gln Gln Asn Lys Glu Tyr Cys Ser Lys
                 85                  90                  95

Glu Gly His Ile Leu Ile Glu Cys Gly Ala Pro Arg Asn Gln Gly Lys
            100                 105                 110

Arg Ser Asp Leu Ser Thr Ala Val Ser Thr Leu Leu Glu Thr Gly Ser
            115                 120                 125

Leu Val Thr Val Ala Glu Gln Phe Pro Val Thr Tyr Val Arg Asn Phe
130                 135                 140

Arg Gly Leu Ala Glu Leu Leu Lys Val Ser Gly Lys Met Gln Gln Arg
145                 150                 155                 160

Asp Trp Lys Thr Ala His Val Ile Val Gly Pro Pro Gly Cys Gly
            165                 170                 175

Lys Ser Gln Trp Ala Arg Asn Phe Ala Glu Pro Arg Asp Thr Tyr Trp
            180                 185                 190

Lys Pro Ser Arg Asn Lys Trp Trp Asp Gly Tyr His Gly Glu Glu Val
            195                 200                 205

Val Val Leu Asp Asp Phe Tyr Gly Trp Leu Pro Trp Asp Asp Leu Leu
210                 215                 220

Arg Leu Cys Asp Arg Tyr Pro Leu Thr Val Glu Thr Lys Gly Gly Thr
225                 230                 235                 240

Val Pro Phe Leu Ala Arg Ser Ile Leu Ile Thr Ser Asn Gln Ala Pro
            245                 250                 255

Gln Glu Trp Tyr Ser Ser Thr Ala Val Pro Ala Val Glu Ala Leu Tyr
            260                 265                 270

Arg Arg Ile Thr Thr Leu Gln Phe Trp Lys Thr Ala Gly Glu Gln Ser
            275                 280                 285

Thr Glu Val Pro Glu Gly Arg Phe Glu Ala Val Asp Pro Pro Cys Ala
            290                 295                 300

Leu Phe Pro Tyr Lys Ile Asn Tyr
305                 310

<210> SEQ ID NO 5
<211> LENGTH: 233
<212> TYPE: PRT
<213> ORGANISM: Porcine Circovirus Type II

<400> SEQUENCE: 5

Met Thr Tyr Pro Arg Arg Arg Tyr Arg Arg Arg Arg His Arg Pro Arg
  1               5                  10                  15

Ser His Leu Gly Gln Ile Leu Arg Arg Arg Pro Trp Leu Val His Pro
                 20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Val Lys Arg Thr Thr Val Thr Thr
        50                  55                  60

Pro Ser Trp Ala Val Asp Met Met Arg Phe Lys Ile Asp Asp Phe Val
 65                  70                  75                  80

Pro Pro Gly Gly Gly Thr Asn Lys Ile Ser Ile Pro Phe Glu Tyr Tyr
                 85                  90                  95

Arg Ile Arg Lys Val Lys Val Glu Phe Trp Pro Cys Ser Pro Ile Thr
            100                 105                 110
```

```
Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Gly Asn
                180                 185                 190

Val Asp His Val Gly Leu Gly Thr Ala Phe Glu Asn Ser Lys Tyr Asp
            195                 200                 205

Gln Asp Tyr Asn Ile Arg Val Thr Met Tyr Val Gln Phe Arg Glu Phe
210                 215                 220

Asn Leu Lys Asp Pro Pro Leu Glu Pro
225                 230

<210> SEQ ID NO 6
<211> LENGTH: 233
<212> TYPE: PRT
<213> ORGANISM: Porcine Circovirus Type I

<400> SEQUENCE: 6

Met Thr Trp Pro Arg Arg Arg Tyr Arg Arg Arg Thr Arg Pro Arg
  1               5                  10                  15

Ser His Leu Gly Asn Ile Leu Arg Arg Arg Pro Tyr Leu Ala His Pro
                20                  25                  30

Ala Phe Arg Asn Arg Tyr Arg Trp Arg Arg Lys Thr Gly Ile Phe Asn
            35                  40                  45

Ser Arg Leu Ser Thr Glu Phe Val Leu Thr Ile Lys Gly Gly Tyr Ser
 50                  55                  60

Gln Pro Ser Trp Asn Val Asn Tyr Leu Lys Phe Asn Ile Gly Gln Phe
 65                  70                  75                  80

Leu Pro Pro Ser Gly Gly Thr Asn Pro Leu Pro Leu Pro Phe Gln Tyr
                85                  90                  95

Tyr Arg Ile Arg Lys Ala Lys Tyr Glu Phe Tyr Pro Arg Asp Pro Ile
                100                 105                 110

Thr Ser Asn Gln Arg Gly Val Gly Ser Thr Val Val Ile Leu Asp Ala
        115                 120                 125

Asn Phe Val Thr Pro Ser Thr Asn Leu Ala Tyr Asp Pro Tyr Ile Asn
130                 135                 140

Tyr Ser Ser Arg His Thr Ile Arg Gln Pro Phe Thr Tyr His Ser Arg
145                 150                 155                 160

Tyr Phe Thr Pro Lys Pro Glu Leu Asp Gln Thr Ile Asp Trp Phe His
                165                 170                 175

Pro Asn Asn Lys Arg Asn Gln Leu Trp Leu His Leu Asn Thr His Thr
                180                 185                 190

Asn Val Glu His Thr Gly Leu Gly Tyr Ala Leu Gln Asn Ala Ala Thr
            195                 200                 205

Ala Gln Asn Tyr Val Val Arg Leu Thr Ile Tyr Val Gln Phe Arg Glu
210                 215                 220

Phe Ile Leu Lys Asp Pro Leu Asn Lys
225                 230

<210> SEQ ID NO 7
```

-continued

```
<211> LENGTH: 59
<212> TYPE: PRT
<213> ORGANISM: Porcine Circovirus Type II

<400> SEQUENCE: 7

Met Lys Cys Thr Leu Val Phe Gln Ser Arg Phe Cys Ile Phe Pro Leu
  1               5                  10                  15

Thr Phe Lys Ser Ser Ala Ser Pro Arg Lys Phe Leu Thr Asn Val Thr
             20                  25                  30

Gly Cys Cys Phe Ala Thr Val Thr Arg Ile Pro Leu Ser Asn Lys Val
         35                  40                  45

Leu Thr Ala Val Asp Arg Ser Leu Arg Cys Pro
     50                  55

<210> SEQ ID NO 8
<211> LENGTH: 115
<212> TYPE: PRT
<213> ORGANISM: Porcine Circovirus Type I

<400> SEQUENCE: 8

Met Thr Cys Thr Ala Val Phe Gln Ser Arg Cys Cys Ile Phe Pro Leu
  1               5                  10                  15

Thr Phe Lys Ser Ser Ala Ser Pro Arg Lys Phe Leu Thr Tyr Val Thr
             20                  25                  30

Gly Asn Cys Ser Ala Thr Val Thr Lys Asp Pro Val Ser Lys Arg Val
         35                  40                  45

Leu Thr Ala Val Asp Arg Ser Leu Arg Phe Pro Trp Phe Arg Gly Ala
     50                  55                  60

Pro His Ser Ile Ser Met Trp Pro Ser Leu Leu Gln Tyr Ser Leu Phe
 65                  70                  75                  80

Cys Trp Ser Val Pro Phe Ala Phe Ser Met Trp Gln Arg Ala Pro Lys
                 85                  90                  95

Tyr His Phe Thr Leu Leu Lys Val Cys Phe Leu Ala Lys Phe Ala Asn
            100                 105                 110

Pro Trp Arg
        115

<210> SEQ ID NO 9
<211> LENGTH: 104
<212> TYPE: PRT
<213> ORGANISM: Porcine Circovirus Type II

<400> SEQUENCE: 9

Met Val Thr Ile Pro Pro Leu Val Phe Arg Trp Phe Pro Val Cys Gly
  1               5                  10                  15

Phe Arg Val Cys Lys Ile Ser Ser Pro Phe Ala Phe Thr Thr Pro Arg
             20                  25                  30

Trp Pro His Asn Glu Val Tyr Ile Gly Phe Pro Ile Thr Leu Leu His
         35                  40                  45

Phe Pro Ala His Phe Gln Lys Phe Ser Gln Pro Ala Glu Ile Phe Asp
     50                  55                  60

Lys Arg Tyr Arg Val Leu Leu Cys Asn Gly His Gln Asn Pro Ala Leu
 65                  70                  75                  80

Gln Gln Gly Thr His Ser Ser Arg Gln Val Thr Pro Leu Ser Leu Arg
                 85                  90                  95

Ser Arg Ser Ser Thr Phe Asn Lys
            100
```

-continued

<210> SEQ ID NO 10
<211> LENGTH: 206
<212> TYPE: PRT
<213> ORGANISM: Porcine Circovirus Type I

<400> SEQUENCE: 10

Met Ile Ser Ile Pro Pro Leu Ile Ser Thr Arg Leu Pro Val Gly Val
1               5                   10                  15

Pro Arg Leu Ser Lys Ile Thr Gly Pro Leu Ala Leu Pro Thr Thr Gly
            20                  25                  30

Arg Ala His Tyr Asp Val Tyr Ser Cys Leu Pro Ile Thr Leu Leu His
        35                  40                  45

Leu Pro Ala His Phe Gln Lys Phe Ser Gln Pro Ala Glu Ile Ser His
    50                  55                  60

Ile Arg Tyr Arg Glu Leu Leu Gly Tyr Ser His Gln Arg Pro Arg Leu
65                  70                  75                  80

Gln Lys Gly Thr His Ser Ser Arg Gln Val Ala Ala Leu Pro Leu Val
                85                  90                  95

Pro Arg Ser Ser Thr Leu Asp Lys Tyr Val Ala Phe Phe Thr Ala Val
            100                 105                 110

Phe Phe Ile Leu Leu Val Gly Ser Phe Arg Phe Leu Asp Val Ala Ala
        115                 120                 125

Gly Thr Lys Ile Pro Leu His Leu Val Lys Ser Leu Leu Leu Ser Lys
    130                 135                 140

Ile Arg Lys Pro Leu Glu Val Arg Ser Ser Thr Leu Phe Gln Thr Phe
145                 150                 155                 160

Leu Ser Ala Asn Lys Ile Ile Lys Lys Gly Asp Trp Lys Leu Pro Tyr
                165                 170                 175

Phe Val Phe Leu Leu Leu Gly Arg Ile Ile Lys Gly Glu His Pro Pro
            180                 185                 190

Leu Met Gly Leu Arg Ala Ala Phe Leu Ala Trp His Phe His
        195                 200                 205

<210> SEQ ID NO 11
<211> LENGTH: 1768
<212> TYPE: DNA
<213> ORGANISM: Porcine Circovirus Type II

<400> SEQUENCE: 11
accagcgcac ttcggcagcg gcagcacctc ggcagcacct cagcagcaac atgcccagca 60
agaagaatgg aagaagcgga ccccaaccac ataaaaggtg ggtgttcacg ctgaataatc 120
cttccgaaga caagcgcaag aaaatacggg agctcccaat ctccctattt gattatttta 180
ttgttggcga ggagggtaat gaggaaggac gaacacctca cctccagggg ttcgctaatt 240
ttgtgaagaa gcaaactttt aataaagtga agtggtattt gggtgcccgc tgccacatcg 300
agaaagccaa aggaactgat cagcagaata aagaatattg cagtaaagaa ggcaacttac 360
ttattgaatg tggagctcct cgatctcaag gacaacggag tgacctgtct actgctgtga 420
gtaccttgtt ggagagcggg attctggtga ccgttgcaaa gcagcaccct gtaacgtttg 480
tcaaaaattt ccgcgggctg gctgaacttt tgaaagtgag cgggaaaatg caaaagcgtg 540
attggaaaac caatgtacac ttcattgtgg ggccacctgg gtgtggtaaa agcaaatggg 600
ctgctaattt tgcaaacccg gaaaccacat actggaaacc acctaaaaac aagtggtggg 660
atggttacca tggtgaaaaa gtggttgtta ttgatgactt ttatggctgg ctgccgtggg 720

```
atgatctact gaaactgtgt gatcgatatc cattgactgt aaaaactaaa ggtggaactg    780 taccttttt  ggcccgcagt attctgatta ccagcaatca gaccccgttg aatggtact    840 cctcaactgc tgtcccagct gtagaagctc tctatcggag gattacttcc ttggtatttt   900
ggaagaatgc tacagaacaa tccacggagg aaggggggcca gtttgtcacc ctttcccccc  960
catgccctga atttccatat gaaataaatt actgagtctt ttttatcact tcgtaatggt   1020
ttttattatt catttagggt ttaagtgggg ggtcttttaag attaaattct ctgaattgta  1080
catacatggt tacacggata ttgtagtcct ggtcgtattt actgttttcg aacgcagtgc   1140
cgaggcctac gtggtccaca tttccagagg tttgtagcct cagccaaagc tgattccttt   1200
tgttatttgg ttggaagtaa tcaatagtgg agtcaagaac aggtttgggt gtgaagtaac   1260
gggagtggta ggagaagggt tgggggattg tatggcggga ggagtagttt acatatgggt   1320
cataggttag ggctgtggcc tttgttacaa agttatcatc taaaataaca gcagtggagc   1380
ccactcccct atcaccctgg gtgatggggg agcagggcca gaattcaacc ttaacctttc   1440
ttattctgta gtattcaaag ggtatagaga ttttgttggt ccccctccc ggggggaacaa   1500 agtcgtcaat tttaaatctc atcatgtcca ccgcccagga gggcgttgtg actgtggtac   1560
gcttgacagt atatccgaag gtgcgggaga ggcgggtgtt gaagatgcca ttttccttc    1620 tccaacggta gcggtggcgg gggtggacga gccaggggcg gcggcggagg atctggccaa   1680
gatggctgcg ggggcggtgt cttcttctgc ggtaacgcct ccttggatac gtcatagctg   1740
aaaacgaaag aagtgcgctg taagtatt                                      1768

<210> SEQ ID NO 12
<211> LENGTH: 240
<212> TYPE: DNA
<213> ORGANISM: Porcine Circovirus Type II

<400> SEQUENCE: 12
accagcgcac ttcggcagcg gcagcacctc ggcagcacct cagcaacaac atgcccagca    60
agaagaatgg aagaagcgga ccccaaccac ataaaaggtg ggtgttcacg ctgaataatc    120
cttccgaaga caagcgcaag aaaatacggg agctcccaat ctccctattt gattattta    180 ttgttggcga ggagggtaat gaggaaggac gaacacctca cctccagggg ttcgctaatt   240

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Loop primer

<400> SEQUENCE: 13
actacagcag cgcacttc                                                 18

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: 1000(-)
      primer

<400> SEQUENCE: 14
aaaaaagact cagtaattta tttcatatgg                                    30

<210> SEQ ID NO 15
```

-continued

<211> LENGTH: 23
<212> TYPE: DNA
<213> ORGANISM: Artificial Sequence
<220> FEATURE:
<223> OTHER INFORMATION: Description of Artificial Sequence: RIF(-) primer

<400> SEQUENCE: 15
atcacttcgt aatggttttt att 23

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: 1710(+) primer

<400> SEQUENCE: 16
tgcggtaacg cctccttg 18

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: 850(-) primer

<400> SEQUENCE: 17
ctacagctgg gacagcagtt g 21

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: 1100(+) primer

<400> SEQUENCE: 18
catacatggt tacacggata ttg 23

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: 1570(-) primer

<400> SEQUENCE: 19
ccgcaccttc ggatatactg 20

<210> SEQ ID NO 20
<211> LENGTH: 59
<212> TYPE: PRT
<213> ORGANISM: Porcine Circovirus Type II

<400> SEQUENCE: 20

```
Met Tyr Thr Ser Leu Trp Gly His Leu Gly Val Val Lys Ala Asn Gly
  1               5                  10                  15

Leu Leu Ile Leu Gln Thr Arg Lys Pro His Thr Gly Asn His Leu Lys
             20                  25                  30

Thr Ser Gly Gly Met Val Thr Met Val Lys Lys Trp Leu Leu Leu Met
         35                  40                  45
```

-continued

```
Thr Phe Met Ala Gly Cys Arg Gly Met Ile Tyr
     50                  55

<210> SEQ ID NO 21
<211> LENGTH: 53
<212> TYPE: PRT
<213> ORGANISM: Porcine Circovirus Type II

<400> SEQUENCE: 21

Met Val Phe Ile Ile His Leu Gly Phe Lys Trp Gly Val Phe Lys Ile
 1               5                  10                  15

Lys Phe Ser Glu Leu Tyr Ile His Gly Tyr Thr Asp Ile Val Val Leu
             20                  25                  30

Val Val Phe Thr Val Phe Glu Arg Ser Ala Glu Ala Tyr Val Val His
         35                  40                  45

Ile Ser Arg Gly Leu
     50

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: 1230(-)
      primer

<400> SEQUENCE: 22
tcccgttact tcacacccaa                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: 400(+)
      primer

<400> SEQUENCE: 23
cctgtctact gctgtgagta                                              20

<210> SEQ ID NO 24
<211> LENGTH: 1343
<212> TYPE: DNA
<213> ORGANISM: Porcine Circovirus Type II

<400> SEQUENCE: 24
ttgttggaga gcgggattct ggtgaccgtt gcaaagcagc accctgtaac gtttgtcaaa    60
aatttccgcg ggctggctga acttttgaaa gtgagcggga aaatgcaaaa gcgtgattgg   120
aaaaccaatg tacacttcat tgtggggcca cctgggtgtg gtaaaagcaa atgggctgct   180
aattttgcaa acccggaaac cacatactgg aaaccaccta aaacaagtg gtgggatggt   240 taccatggtg aaaaagtggt tgttattgat gactttatg gctggctgcc gtgggatgat   300
ctactgaaac tgtgtgatcg atatccattg actgtaaaaa ctaaaggtgg aactgtacct   360
tttttggccc gcagtattct gattaccagc aatcaaaccc cgttggaatg gtactcctca   420
actgctgtcc cagctgtaga agctctctat cggaggatta cttccttggt attttggaag   480
aatgttacag aacaatccac ggaggaaggg ggccagtttg tcacccttc cccccatgc    540 cctgaatttc catatgaaat aaattactga gtcttttta tcacttcgta atggttttta   600
ttattcattt agggtttaag tgggggggtct ttaagattaa attctctgaa ttgtacatac   660
```

-continued

```
atggttacac ggatattgta gtcctggtcg tatttactgt tttcgaacgc agtgccgagg    720
cctacgtggt ccacatttct agaggtttgt agcctcagcc aaagctgatt ccttttgtta    780
tttggttgga agtaatcaat agtggagtca agaacaggtt tgggtgtgaa gtaacgggag    840
tggtaggaga agggttgggg gattgtatgg cgggaggagt agtttacata tgggtcatag    900
gttagggctg tggcctttgt tacaaagtta tcatctagaa taacagcagt ggagcccact    960
cccctatcac cctgggtgat gggggagcag ggccagaatt caaccttaac ctttcttatt   1020
ctgtagtatt caaagggtat agagattttg ttggtccccc ctcccggggg aacaaagtcg   1080
tcaatattaa atctcatcat gtccaccgcc caggagggcg ttgtgactgt ggtagccttg   1140
acagtatatc cgaaggtgcg ggagaggcgg gtgttgaaga tgccattttt ccttctccaa   1200
cggtagcggt ggcgggggtg gacgagccag gggcggcggc ggaggatctg gccaagatgg   1260
ctgcgggggc ggtgtcttct tctgcggtaa cgcctccttg gatacgtcat agctgaaaac   1320
gaaagaagtg cgctgtaagt att                                            1343
```